(12) United States Patent
Thompson-Nauman et al.

(10) Patent No.: US 11,344,737 B2
(45) Date of Patent: May 31, 2022

(54) IMPLANTABLE CARDIOVERTER-DEFIBRILLATOR (ICD) SYSTEM INCLUDING SUBSTERNAL LEAD

(71) Applicant: Medtronic, Inc., Minneapolis, MN (US)

(72) Inventors: Amy E. Thompson-Nauman, Ham Lake, MN (US); Melissa G. T. Christie, Andover, MN (US); Paul J. DeGroot, Shoreview, MN (US); Rick D. McVenes, Isanti, MN (US); Becky L. Dolan, Chisago, MN (US)

(73) Assignee: Medtronic, Inc., Minneapolis, MN (US)

( * ) Notice: Subject to any disclaimer, the term of this patent is extended or adjusted under 35 U.S.C. 154(b) by 61 days.

(21) Appl. No.: 16/678,365

(22) Filed: Nov. 8, 2019

(65) Prior Publication Data
US 2020/0069952 A1 Mar. 5, 2020

Related U.S. Application Data

(62) Division of application No. 14/261,470, filed on Apr. 25, 2014, now Pat. No. 10,471,267.
(Continued)

(51) Int. Cl.
*A61N 1/39* (2006.01)
*A61N 1/05* (2006.01)

(52) U.S. Cl.
CPC .......... *A61N 1/39622* (2017.08); *A61N 1/05* (2013.01); *A61N 1/3956* (2013.01)

(58) Field of Classification Search
CPC ..... A61N 1/39622; A61N 1/05; A61N 1/3956
See application file for complete search history.

(56) References Cited

U.S. PATENT DOCUMENTS

| 3,614,954 A | 10/1971 | Mirowski et al. |
| 3,706,313 A | 12/1972 | Milani et al. |
(Continued)

FOREIGN PATENT DOCUMENTS

| CN | 1859870 A | 11/2006 |
| CN | 102858403 A | 1/2013 |
(Continued)

OTHER PUBLICATIONS

Preliminary Amendment from U.S. Appl. No. 16/725,458, dated Mar. 25, 2020, 7 pp.
(Continued)

*Primary Examiner* — Mark W. Bockelman
(74) *Attorney, Agent, or Firm* — Shumaker & Sieffert, P.A.

(57) ABSTRACT

Substernal implantable cardioveter-defibrillator (ICD) systems and methods for providing substernal electrical stimulation therapy to treat malignant tachyarrhythmia, e.g., ventricular tachycardia (VT) and ventricular fibrillation (VF) are described. In one example, an implantable cardioveter-defibrillator (ICD) system includes an ICD implanted in a patient and an implantable medical electrical lead. The lead includes an elongated lead body having a proximal end and a distal portion, a connector at the proximal end of the lead body configured to couple to the ICD, and one or more electrodes along the distal portion of the elongated lead body. The distal portion of the elongated lead body of the lead is implanted substantially within an anterior mediastinum of the patient and the ICD is configured to deliver electrical stimulation to a heart of the patient using the one or more electrodes.

20 Claims, 8 Drawing Sheets

Related U.S. Application Data

(60) Provisional application No. 61/819,997, filed on May 6, 2013.

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |
| 4,270,549 A | 6/1981 | Heilman |
| 4,280,510 A | 7/1981 | O'Neill |
| 4,291,707 A | 9/1981 | Heilman et al. |
| 4,437,475 A | 3/1984 | White |
| 4,450,527 A | 5/1984 | Sramek |
| 4,512,351 A | 4/1985 | Pohndorf |
| 4,538,624 A | 9/1985 | Tarjan |
| 4,693,253 A | 9/1987 | Adams |
| 4,708,145 A | 11/1987 | Tacker, Jr. et al. |
| 4,765,341 A | 8/1988 | Mower et al. |
| 4,787,389 A | 11/1988 | Tarjan |
| 4,832,687 A | 5/1989 | Smith, III |
| 4,865,037 A | 9/1989 | Chin et al. |
| 4,953,551 A | 9/1990 | Mehra et al. |
| 5,036,854 A | 8/1991 | Schollmeyer et al. |
| 5,099,838 A | 3/1992 | Bardy |
| 5,105,810 A | 4/1992 | Collins et al. |
| 5,113,869 A | 5/1992 | Nappholz et al. |
| 5,125,904 A | 6/1992 | Lee |
| 5,129,392 A | 7/1992 | Bardy et al. |
| 5,176,135 A | 1/1993 | Fain et al. |
| 5,193,540 A | 3/1993 | Schulman et al. |
| 5,203,348 A | 4/1993 | Dahl et al. |
| 5,255,691 A | 10/1993 | Otten |
| 5,255,692 A | 10/1993 | Neubauer et al. |
| 5,261,400 A | 11/1993 | Bardy |
| 5,273,053 A | 12/1993 | Pohndorf |
| 5,292,338 A | 3/1994 | Bardy |
| 5,300,106 A | 4/1994 | Dahl et al. |
| 5,312,355 A | 5/1994 | Lee |
| 5,331,966 A | 7/1994 | Bennett et al. |
| 5,336,252 A | 8/1994 | Cohen |
| 5,342,407 A | 8/1994 | Dahl et al. |
| 5,366,496 A | 11/1994 | Dahl et al. |
| 5,376,105 A | 12/1994 | Hedberg |
| 5,385,574 A | 1/1995 | Hauser et al. |
| 5,411,539 A | 5/1995 | Neisz |
| 5,423,326 A | 6/1995 | Wang et al. |
| 5,439,484 A | 8/1995 | Mehra |
| 5,441,504 A | 8/1995 | Pohndorf et al. |
| 5,456,699 A | 10/1995 | Armstrong |
| 5,468,254 A | 11/1995 | Hahn et al. |
| 5,476,493 A | 12/1995 | Muff |
| 5,509,924 A | 4/1996 | Paspa et al. |
| 5,534,018 A | 7/1996 | Wahlstrand et al. |
| 5,534,022 A | 7/1996 | Hoffmann et al. |
| 5,601,607 A | 2/1997 | Adams |
| 5,603,732 A | 2/1997 | Dahl et al. |
| 5,613,953 A | 3/1997 | Pohndorf |
| 5,690,648 A | 11/1997 | Fogarty et al. |
| 5,721,597 A | 2/1998 | Kakinuma et al. |
| 5,800,465 A | 9/1998 | Thompson et al. |
| 5,944,732 A | 8/1999 | Raulerson et al. |
| 5,951,518 A | 9/1999 | Licata et al. |
| 5,951,593 A | 9/1999 | Lu et al. |
| 6,032,079 A | 2/2000 | Knight et al. |
| 6,040,082 A | 3/2000 | Haas et al. |
| 6,059,750 A | 5/2000 | Fogarty |
| 6,091,989 A | 7/2000 | Swerdlow et al. |
| 6,095,987 A | 8/2000 | Shmulewitz et al. |
| 6,104,957 A | 8/2000 | Ala et al. |
| 6,120,431 A | 9/2000 | Magovern |
| 6,122,552 A | 9/2000 | Tockman et al. |
| 6,159,198 A | 12/2000 | Gardeski et al. |
| 6,228,052 B1 | 5/2001 | Pohndorf |
| 6,324,414 B1 | 11/2001 | Gibbons et al. |
| 6,415,187 B1 | 7/2002 | Kuzma et al. |
| 6,445,954 B1 | 9/2002 | Olive et al. |
| 6,544,247 B1 | 4/2003 | Gardeski et al. |
| 6,721,597 B1 | 4/2004 | Bardy et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,856,835 B2 | 2/2005 | Bardy et al. |
| 6,866,044 B2 | 3/2005 | Bardy et al. |
| 6,868,291 B1 | 3/2005 | Bonner et al. |
| 6,887,229 B1 | 5/2005 | Kurth |
| 6,890,295 B2 | 5/2005 | Michels et al. |
| 6,999,819 B2 | 2/2006 | Swoyer et al. |
| 7,033,326 B1 | 4/2006 | Pianca et al. |
| 7,050,851 B2 | 5/2006 | Plombon et al. |
| 7,069,083 B2 | 6/2006 | Finch et al. |
| 7,096,064 B2 | 8/2006 | Deno et al. |
| 7,117,039 B2 | 10/2006 | Manning et al. |
| 7,195,637 B2 | 3/2007 | Mika |
| 7,218,970 B2 | 5/2007 | Ley et al. |
| 7,225,034 B2 | 5/2007 | Ries et al. |
| 7,229,450 B1 | 6/2007 | Chitre et al. |
| 7,272,448 B1 | 9/2007 | Morgan et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,369,899 B2 | 5/2008 | Malinowski et al. |
| 7,389,134 B1 | 6/2008 | Karicherla et al. |
| 7,392,085 B2 | 6/2008 | Warren et al. |
| 7,450,997 B1 | 11/2008 | Pianca et al. |
| 7,496,408 B2 | 2/2009 | Ghanem et al. |
| 7,499,758 B2 | 3/2009 | Cates et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,684,864 B2 | 3/2010 | Olson et al. |
| 7,736,330 B2 | 6/2010 | Bardy |
| 7,761,150 B2 | 7/2010 | Ghanem et al. |
| 7,765,014 B2 | 7/2010 | Eversull et al. |
| 7,801,622 B2 | 9/2010 | Camps et al. |
| 7,837,671 B2 | 11/2010 | Eversull et al. |
| 7,846,088 B2 | 12/2010 | Ness |
| 7,850,610 B2 | 12/2010 | Ferek-Petric |
| 7,890,191 B2 | 2/2011 | Rutten et al. |
| 7,908,015 B2 | 3/2011 | Lazeroms et al. |
| 7,920,915 B2 | 4/2011 | Mann et al. |
| 7,930,028 B2 | 4/2011 | Lang et al. |
| 7,930,040 B1 | 4/2011 | Kelsch et al. |
| 7,983,765 B1 | 7/2011 | Doan et al. |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,165,696 B2 | 4/2012 | McClure et al. |
| 8,260,436 B2 | 9/2012 | Gerber et al. |
| 8,280,527 B2 | 10/2012 | Eckerdal et al. |
| 8,340,779 B2 | 12/2012 | Harris et al. |
| 8,355,786 B2 | 1/2013 | Malinowski |
| 8,386,052 B2 | 2/2013 | Harris et al. |
| 8,394,079 B2 | 3/2013 | Drake et al. |
| 8,435,208 B2 | 5/2013 | Bardy |
| 8,442,620 B2 | 5/2013 | Silipo et al. |
| 8,452,421 B2 | 5/2013 | Thenuwara et al. |
| 8,478,424 B2 | 7/2013 | Tronnes |
| 8,478,426 B2 | 7/2013 | Barker |
| 8,594,809 B2 | 11/2013 | Yang et al. |
| 8,686,052 B2 | 4/2014 | Niitsu et al. |
| 8,886,311 B2 | 11/2014 | Anderson et al. |
| 9,126,031 B2 | 9/2015 | Tekmen et al. |
| 9,717,923 B2 | 8/2017 | Thompson-Nauman et al. |
| 10,471,267 B2 | 11/2019 | Thompson-Nauman et al. |
| 10,525,272 B2 | 1/2020 | Thompson-Nauman et al. |
| 10,532,203 B2 | 1/2020 | Thompson-Nauman et al. |
| 10,556,117 B2 | 2/2020 | Thompson-Nauman et al. |
| 10,668,702 B2 | 6/2020 | Yang et al. |
| 10,688,270 B2 | 6/2020 | Sims et al. |

(56) References Cited

U.S. PATENT DOCUMENTS

| | | |
|---|---|---|
| 2002/0049476 A1 | 4/2002 | Bardy et al. |
| 2002/0120294 A1 | 8/2002 | Kroll |
| 2003/0088278 A1 | 5/2003 | Bardy et al. |
| 2003/0114908 A1 | 6/2003 | Flach |
| 2004/0059348 A1 | 3/2004 | Geske et al. |
| 2004/0102829 A1 | 5/2004 | Bonner et al. |
| 2004/0143284 A1 | 7/2004 | Chin |
| 2004/0210293 A1 | 10/2004 | Bardy et al. |
| 2004/0215240 A1 | 10/2004 | Lovett et al. |
| 2004/0215308 A1 | 10/2004 | Bardy et al. |
| 2004/0230279 A1 | 11/2004 | Cates et al. |
| 2004/0230280 A1 | 11/2004 | Cates et al. |
| 2004/0230281 A1 | 11/2004 | Heil et al. |
| 2004/0230282 A1 | 11/2004 | Cates et al. |
| 2004/0236396 A1 | 11/2004 | Coe et al. |
| 2005/0049663 A1 | 3/2005 | Harris et al. |
| 2005/0131505 A1 | 6/2005 | Yokoyama |
| 2005/0277990 A1 | 12/2005 | Ostroff et al. |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0136004 A1 | 6/2006 | Cowan et al. |
| 2006/0161205 A1 | 7/2006 | Mitrani et al. |
| 2006/0247753 A1 | 11/2006 | Wenger et al. |
| 2006/0253181 A1 | 11/2006 | Schulman et al. |
| 2006/0265018 A1 | 11/2006 | Smith et al. |
| 2007/0023947 A1 | 2/2007 | Ludwig et al. |
| 2007/0049975 A1 | 3/2007 | Cates et al. |
| 2007/0088394 A1 | 4/2007 | Jacobson |
| 2007/0100409 A1 | 5/2007 | Worley et al. |
| 2007/0179388 A1 | 8/2007 | Larik et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2009/0270962 A1 | 10/2009 | Yang et al. |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0042108 A1 | 2/2010 | Hibino |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0152798 A1 | 6/2010 | Sanghera et al. |
| 2010/0211064 A1 | 8/2010 | Mahapatra et al. |
| 2010/0217298 A1 | 8/2010 | Bardy |
| 2010/0217301 A1 | 8/2010 | Bardy |
| 2010/0241185 A1 | 9/2010 | Mahapatra et al. |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0077708 A1 | 3/2011 | Ostroff |
| 2011/0125163 A1 | 5/2011 | Rutten et al. |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0123496 A1 | 5/2012 | Schotzko et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2012/0209286 A1 | 8/2012 | Papay et al. |
| 2012/0220849 A1 | 8/2012 | Brockway et al. |
| 2012/0316613 A1 | 12/2012 | Keefe et al. |
| 2013/0041345 A1 | 2/2013 | Kilcoin et al. |
| 2013/0103049 A1 | 4/2013 | Bonde |
| 2013/0158564 A1 | 6/2013 | Harris et al. |
| 2013/0238067 A1 | 9/2013 | Baud ina |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330329 A1 | 11/2014 | Thompson-Nauman et al. |
| 2014/0330331 A1 | 11/2014 | Thompson-Nauman et al. |
| 2020/0069952 A1 | 3/2020 | Thompson-Nauman et al. |
| 2020/0129755 A1 | 4/2020 | Thompson-Nauman et al. |
| 2020/0147402 A1 | 5/2020 | Thompson-Nauman et al. |
| 2020/0289816 A1 | 9/2020 | Thompson-Nauman et al. |

FOREIGN PATENT DOCUMENTS

| | | |
|---|---|---|
| EP | 0347353 A1 | 12/1989 |
| EP | 1541191 | 6/2005 |
| FR | 2773491 A1 | 7/1999 |
| JP | 2007500549 A | 1/2007 |
| WO | 9938568 A1 | 8/1999 |
| WO | 2001023035 A1 | 4/2001 |
| WO | 02242275 A2 | 3/2002 |
| WO | 0226315 A1 | 4/2002 |
| WO | 0241946 A2 | 5/2002 |
| WO | 2004073506 A2 | 9/2004 |
| WO | 2005011809 A2 | 2/2005 |
| WO | 2006060705 A1 | 6/2006 |
| WO | 20100047893 A1 | 4/2010 |

OTHER PUBLICATIONS

Ganapathy et al., ""Implantable Device to Monitor Cardiac Activity with Sternal Wires,"" Pace, vol. 37, Dec. 2014, 11 pages.

Guenther et al., ""Substernal Lead Implantation: A Novel Option to Manage OFT Failure in S-ICD patients,"" Clinical Research Cardiology, Published On-line Oct. 2, 2014, 3 pages.

Tung et al., ""Initial Experience Of Minimal Invasive Extra Cardiac Placement Of High Voltage Defibrillator Leads,"" Canadian Cardiovascular Congress 2007, Oct. 2007, vol. 23, Supplement SC, Abstract 0697, http://www.pulsus.com/ccc2007/abs/0697.htm, 2 pages.

(PCT/US2014/036786) PCT Notification of Transmittal of the International Search Report and the Written Opinion of the International Searching Authority, dated Jul. 29, 2014, 10 pages.

Obadia, et al., "New Approach for Implantation of Automatic Defibrillators Using Videothoracoscopy", Journal Ann Cardiel Angeiol (Paris); Sep. 1994; 43 (7) Abstract Only, 1 page.

Lemmer, "Defibrillator Patch Constriction, Letter to the Editor", The Annals of Thoracic Surgery, 1996, 1 page.

Ely et al., "Thoracoscopic Implantation of the Implantable Cardioverter Defibrillator", Minimally Invasive Techniques; (Can be found on the World-Wide Web at http://chestiournal.chestpubs.org on May 6, 2013); dated Jan. 1993; 2 pages.

Damiano, "Implantation of Cardioverter Defibrillators in the Post-Sternotomy Patient", The Annals of Thoracic Surgery, 1992; 53: pp. 978-983.

Piccione, et al., "Erosion of ExtrapericardialImplantable Cardioverter Defibrillator Patch Through the Gastic Fundus with Fistulous Tract Information", Cardiology in Review; 2006; 14, e21-e23 pages.

Vyhmeister et al., "Simple Approach for Extrapericardial Placement of Defibrillator Patches via Median Sternotomy", The Annals of Thoracic Surgery; 1994; 57:4 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

Obadia et al., "Thoracoscopic Approach to Implantable Cardioverter Defibrillator Patch Electrode Implantation", Pacing and Clinical Electrophysiology; Jun. 1996; vol. 19; 6 pages.

Shapira, et al., "A Simplied Method for Implantation of Automatic Cardioverter Defibrillator in Patients with Previous Cardiac Surgery", Pacing and Clinical Electrophysiology, Jan. Part I, 1993, vol. 16; 6 pages.

(56) References Cited

OTHER PUBLICATIONS

Quigley et al., "Migration of an Automatic Implantable Cardioverter-Defibrillator Patch Causing Massive Hemothorax", Journal Texas Heart Institute, Nov. 1, 1996; vol. 23, 4 pages.
Karwande et al., "Bilateral Anterior Thoracotomy for Automatic Implantable Cardioverter Defibrillator Placement in Patients with Previous Sternotomy", The Annals of Thoracic Surgery; Oct. 1992; 54(4); 3 pages.
Bielefeld et al., "Thoracoscopic Placement of Implantable Cardioverter-Defibrillator Patch Leads in Sheep", Circulation; Nov. 1993, vol. 88, No. 5, Part 2; 5 pages.
Frame et al., "Long-Term Stability of Defibrillation Thresholds with Intrapericardial Defibrillator Patches", Pacing and Clinical Electrophysiology, Jan. 1993, Part II, vol. 16, 6 pages.
Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.
Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Bolling et al., "Automatic Internal Cardioverter Defibrillator: A Bridge to Heart Transplantation", Heart Lung Transplantation, Abstract Only, Jul.-Aug. 1991, 1 page.
Steinke et al., "Subepicardial Infarction, Myocardial Impression, and Ventricular Penetration by Sutureless Electrode and Leads", Chest; 70: 1, Jul. 1976, 2 pages.
Avogadros Lab Supply Inc., Catalog; Scoopula with Beech Wood Handle, can be found on-line at http://www.avogadro-lab-supply.com/search.php, accessed Oct. 6, 2013, 1 page.
Medtronic, Inc. 6996SQ Subcutaneous, Unipolar Lead with Defibrillation Coil Electrode, Technicial Manual, 22 pages.
Medtronic, Inc. 6996T Tunneling Tool, Technical Manual, 12 pages.
Pebax Product Brochure, 14 pages and can be found on-line at http://www.pebax.com/export/sites/pebax/.content/medias/downloads/literature/pebax-product-range-brochure. pdf, 14 pages.
Cigna et al., "A New Technique for Substernal Colon Transposition with A Breast Dissector: Report of 39 Cases", Journal of Plastic, Reconstructive and Aesthetic Surgery, 2006:59, 4 pages.
Tung et al.. "Minimal Invasive Extra Cardiac Placement of High Voltage Defibrillator Leads", Poster 3; S200 Abstract, P0-3-4; St. Paul Hospital, Vancouver, British Columbia, Canada, 1 pages.
Molina et al, "An Epicardial Subxiphoid Implantable Defibrillator Lead: Superior Effectiveness After Failure of Slndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
Baudoin et al., "The Superior Epigastric Artery Does Not Pass Through Larrey's Space (Trigonum Sternocostale)", Surgical Radial Anal (2003), 25: 259-262.
Haydin et al., "Subxiphoid Approach to Epicardial Implantation of Implantable Cardioverter Defibrillators in Children", Pace, vol. 36, Aug. 2013, 5 pages.
Falk et al., "External Cardiac Pacing Using Low Impedance Electrodes Suitable for Defibrillation: A Comparative Blinded Study," Journal of American College of Cardiology, vol. 22, No. 5, Nov. 1, 1993,5 pages.
Laudon, M. K., "Pulse Output", Chapter 11 of Design of Pacemakers, Published by the Institute of Electrical and Electronics Engineers, Inc., New York,(1995), 30 pages.
Alexander et al., "Implications of Implantable Cardioverter Defibrillator Therapy in Congenital Heart Disease and Pediatrics," Journal of Cardiovascular Electrophysiology, vol. 15, No. 1, Jan. 2004, 5 pages.
Baddour et al., Update on Cardiovascular Implantable Electronic Device Infections and their Management—A Scientific Statement from the American Heart Association, Circulation available at http://circ.ahajournals.org, Jan. 26, 2010, 23 pages.
Bauersfeld et al., "Initial Experience with Implantable Cardioverter Defibrillator Systems Using Epicardial and Pleural Electrodes in Pediatric Patients," The Annals of Theoracic Surgery, 2007, vol. 84, 3 pages.
Berul et al., "Minmally Invasive Cardioverter Defibrillator Implantation for Children: An Animal Model and Pediatric Case Report," Journal of Pacing and Clinical Electrophysiology, Dec. 2001, vol. 24, No. 12, 6 pages.
Hsia et al., "Novel Minimally Invasive, Intrapericardial Implantable Cardioverter Defibrillator Coil System: A Useful Approach to Arrhythmia Therapy in Children," The Annals of Thoracic Surgery, 2009, vol. 87; 6 pages.
Tung, et al. "Invention Disclosure Form for Hybrid Endovascular and Extrvascular Implantable Cardioverter-Defibrillator System," Mar. 2006, 10 pages.
Copper, et al., "Implantable Cardioverter Defibrillator Lead Complications and Laser Extraction in Children and Young Adults with Congenital Heart Disease: Implications for Implantation and Management," Journal of Cardiovascular Electrophysiology, vol. 14, No. 4, Apr. 2003, 7 pages.
"SQ-RX Pulse Generator, A Component of the S-ICD System, User's Manual, Model 1010," Cameron Health, Inc., Dec. 2, 2008, 46 pp.
Erickson, MD., "Non-thoracotomy ICD Implantation in Pediatric and Adult Congenital Heart Disease Patients," Oct. 2015, 44 slides.
Office Action, in the Chinese language, from Chinese Application No. 201480025740.9, dated Sep. 27, 2016, 9 pp.
First Office Action and Search Report, and translation thereof, from counterpart Chinese Application No. 201480035082.1, dated Sep. 27, 2016, 29 pp.
First Office Action and Search Report, and translation thereof, from counterpart Chinese Application No. 201480025657.1, dated Oct. 8, 2016, 24 pp.
"Electrode Positioning for Reliable Telemetry ECG Recordings During Social Stress in Unrestrained Rats" Sgoifo et al ; Physiology and Behavious, vol. 60, issue 6 Dec. 1996, pp. 1397-1401.
U.S. Appl. No. 16/742,385, filed Jan. 14, 2020 by Thompson-Nauman et al.
U.S. Appl. No. 16/725,458, filed Dec. 23, 2019 by Thompson-Nauman et al.
Prosecution History of Opposition from European Patent No. 1318856, dated Apr. 15, 2015 through Apr. 10, 2017, 312 pp.
Bardy et al., "An Entirely Subcutaneous Implantable Cardioverter-Defibrillator," The New England Journal of Medicine, May 2010, 9 pp.
Bardy et al., "A Simplified, Single-Lead Unipolar Transvenous Cardioversion-Defibrillation System," Circulation, vol. 8, No. 2, Aug. 1993, 5 pp.
"Pharmacological and Electrical Cardioversion of AF," Europace Supplements, vol. 2, Jan. 2001, 1 pp.
Boston Scientific, "Dr. Lucas Boersma Shares Insight into the S-ICD Effortless 3-year Analysis," retrieved from http://www.bostonscientific.com/en-EU/products/defibrillators/s-icd-emblem/clinical-data.html on Nov. 24, 2016, 3 pp.
Bocker et al., "Treatment with implantable defibrillators in childhood," Herzschr Elektrophys, accepted Nov. 11, 1999, 4 pp.
"Emblem S-ICD, Emblem MRI S-ICD," Boston Scientific, REF 4209, A219, Manual 359481-001, Nov. 2015, 72 pp.
Thogersen et al., "Implantable Cardioverter Defibrillator in a 4-Month-Old Infant with Cardiac Arrest Associated with a Vascular Heart Tumor," accepted Jan. 8, 2001, Pace, vol. 24, Nov. 2001, 2 pp.
"St. Jude Medical Announces Filing of PMA Supplement for Ventritex Angstrom MD and Contour MD ICD's," St. Jude Medical, Inc., Jun. 5, 1998, 1 pp.
Fischbach et al., "Use a Single Coil Transvenous Electrode with an Abdominally Placed Implantable Cardioverter Defibrillator in Children," Place, vol. 23, May 2000, 5 pp.
Gradaus et al., "Nonthoracotomy Implantable Cardioverter Defibrillator Placement in Children: Use of Subcutaneous Array Leads and Abdominally Placed Implantable Cardioverter Defibrillators in Children," Journal of Cardiovascular Electrophysiology, vol. 12, No. 3, Mar. 2001, 5 pp.

(56) References Cited

OTHER PUBLICATIONS

Haffajee et al., "A Multicenter, Randomized Trial Comparing an Active Can Implantable Defibrillator with a Passive Can System" Pace, vol. 20, Jan. 1997, Part II, 5 pp.

Hoffmann et al., "experience with pectoral versus abdominal implantation of a small defibrillator," European Heart Journal, vol. 19, Jul. 1998, 14 pp.

Juchem et al., "Successful use of transvenous coil electrodes as single element subcutaneous array leads," published online Jan. 14, 2009, 4 pp.

Kriebel et al., "Implantation of an 'extracardiac' internal cardioverter defibrillator in a 6-month-old infant," Zeitschrift fur Kardiologie, Jan. 18, 2005, 4 pp.

Kuschyk et al., "A Multcenter Study of Shock Pathways for Subcutaneous Implantable Defibrillators," Journal of Cardiovascular Electrophysiology, vol. 25, No. 1, Jan. 2014, 7 pp.

Olson et al., "Onset and Stability for Ventricular Tachyarrhythmia Detection in an Implantable Pacer-Cardioverter-Defibrillator," IEEE, 1987, 4 pp. (Applicant points out, in accordance with MPEP 609.04(a), that the year of publication, 1987, is sufficiently earlier than the effective U.S. filing date, so that the particular month of publication is not in issue.).

Park et al., "Use of an Implantable Cardioverter Defibrillator in an Eight-Moth-Old Infant with Ventricular Fibrillation Arising from a Myocardial Fibroma," Pace, vol. 22, Jan. 1999, Part I, 2 pp.

Schuder et al., "Ventricular Defibrillation in the Dog Using Implanted and Partially Implanted Electrode Systems," The American Journal of Cardiology, vol. 33, Feb. 1974, 5 pp.

Schuder et al., "Experimental Ventricular Defibrillation with an Automatic and Completely Implanted System," Trans. Amer. Soc. Artif. Int. Organs, vol. XVI, 1970, (Applicant points out, in accordance with MPEP 609.04(a), that the year of publication, 1970, is sufficiently earlier than the effective U.S. filing date, so that the particular month of publication is not in issue.).

Schuder, "The Role of an Engineering Oriented Medical Research Group in Developing Improved Methods ad Devices for Achieving Ventricular Defibrillation The University of Missouri Experience," Pace, vol. 16, Jan. 1993, 30 pp.

Weiss et al., Safety and Efficacy of a Totally Subcutaneous Implantable-Cardioverter Defibrillator, Arrhythmia/Electrophysiology, Jun. 28, 2013, 11 pp.

Thompson-Nauman et al., "Implantable Cardioverter-Defibrillator (ICD) System Including Substernal Lead", JP Patent Application No. 2016-512987, Japanese Office Action dated Feb. 2, 2018, 4 pages.

Thompson-Nauman et al., "Implantable Cardioverter-Deflibrillator (ICD) System Including Substernal Lead," Notice of Third Of Office Action, Chinese Patent Application No. 201480025740.9, dated Jan. 2, 2018, 19 pages.

Thompson-Nauman et al., "Implantable Cardioverter-Defibrillator (ICD) System Including Substernal Packing Lead," Notice of Third Office Action, Chinese Patent Application No. 201480035082.1, dated Jan. 2, 2018, 22 pages.

Thompson-Nauman et al., Implantable Cardioverter-Defibrillator (ICD) System Including Substernal Pacing Lead, Notice of Third Office Action, Chinese Patent Application No. 201480025657.1, dated Jan. 2, 2018, 20 pages.

Extended Search Report from counterpart European Application No. 20191170.8, dated Jan. 21, 2021, 7 pp.

Prosecution history from U.S. Appl. No. 14/261,470, dated Apr. 25, 2014, through Oct. 3, 2019, 219 pp.

Prosecution history from U.S. Appl. No. 14/261,488, dated Apr. 25, 2014, through Jan. 27, 2020, 308 pp.

Prosecution history from U.S. Appl. No. 14/261,456, dated Apr. 25, 2014, through Dec. 12, 2019, 223 pp.

Prosecution history from U.S. Appl. No. 14/261,460, dated Apr. 25, 2014, through May 11, 2017, 61 pp.

Prosecution history from U.S. Appl. No. 15/661,365, dated Jul. 27, 2017, through Dec. 9, 2019, 139 pp.

Prosecution history from U.S. Appl. No. 14/261,479, dated Apr. 25, 2014, through Dec. 12, 2019, 139 pp.

Office Action from U.S. Appl. No. 16/725,458, dated Jun. 25, 2021, 6 pp.

Response to Search Report dated Jan. 21, 2021, from counterpart European Application No. 20191170.8, filed Aug. 13, 2021, 17 pp.

Office Action from U.S. Appl. No. 16/742,385, dated Oct. 6, 2021, 8 pp.

Response to Office Action dated Jun. 25, 2021, from U.S. Appl. No. 16/725,458, filed Sep. 27, 2021, 14 pp.

Notice of Allowance from U.S. Appl. No. 16/725,458, dated Jan. 28, 2022, 5 pp.

Office Action from U.S. Appl. No. 16/885,837, dated Dec. 24, 2021, 7 pp.

Response to Office Action dated Oct. 6, 2021, from U.S. Appl. No. 16/742,385, filed Jan. 6, 2022, 11 pp.

Response to Office Action dated Dec. 24, 2021, from U.S. Appl. No. 16/885,837, filed Mar. 24, 2022, 3 pp.

Final Office Action from U.S. Appl. No. 16/742,385, dated Apr. 14, 2022, 8 pp.

Notice of Allowance from U.S. Appl. No. 16/885,837, dated Apr. 12, 2022, 5 pp.

IMPLANTABLE CARDIOVERTER-DEFIBRILLATOR (ICD) SYSTEM INCLUDING SUBSTERNAL LEAD

This application is a divisional of U.S. application Ser. No. 14/261,470, filed on Apr. 25, 2014, which claims the benefit of U.S. Provisional Application No. 61/819,997, filed on May 6, 2013. The entire content of each of these applications is incorporated herein by reference.

FIELD OF THE INVENTION

The present application relates to methods and medical devices for providing an implantable cardioverter defibrillator system including a substernal lead.

BACKGROUND OF THE INVENTION

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter defibrillator (ICD) system has been shown to be beneficial at preventing SCD. An ICD system includes an ICD, which is a battery powered electrical shock device, that may include an electrical housing electrode (sometimes referred to as a can electrode), that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, subcutaneous ICD systems have been devised to provide shocks to the heart without placing electrical lead wires within the heart or attaching electrical wires directly to the heart.

Subcutaneous ICD systems have been devised to deliver shocks to the heart by the use of a defibrillation lead placed subcutaneously on the torso. However, the subcutaneous ICD systems may require an output of around 80 Joules (J) of energy to provide effective defibrillation therapy. As a result, subcutaneous ICDs may require larger batteries and more storage capacitors than transvenous ICDs. As such, the subcutaneous ICDs are generally larger in size than transvenous ICDs. The large size of the subcutaneous ICD may compromise patient comfort, decrease system longevity and/or increase cost of the system. In addition, conventional subcutaneous ICD systems are incapable of delivering antitachycardia pacing (ATP) without extreme discomfort to the patient, which is a standard therapy in transvenous ICDs to terminate lethal tachyarrhythmias without providing a shock.

SUMMARY OF THE INVENTION

The present application advantageously provides implantable substernal ICD systems and methods for providing substernal electrical stimulation therapy to treat malignant tachyarrhythmia, e.g., ventricular tachycardia (VT) and ventricular fibrillation (VF). The substernal electrical stimulation therapy may take the form of shocks (e.g., either cardioversion or defibrillation shocks) or pacing pulses (e.g., ATP, post-shock pacing, or bradycardia pacing). Such an ICD system is thus capable of providing defibrillation or cardioversion shocks and/or pacing pulses without a lead that enters the vasculature, is implanted within the heart, or is attached to the heart.

In one embodiment, an ICD system comprises an ICD implanted subcutaneously in a patient and an implantable medical electrical lead. The implantable medical lead includes an elongated lead body having a proximal end and a distal portion, a connector at the proximal end of the lead body configured to couple to the ICD, and one or more electrodes along the distal portion of the elongated lead body. The distal portion of the elongated lead body of the lead is implanted substantially within an anterior mediastinum of the patient. The ICD is configured to deliver electrical stimulation to a heart of the patient using the one or more electrodes.

In another embodiment, a method comprises detecting a tachycardia with the implantable cardioverter-defibrillator (ICD) system having an ICD and a medical electrical lead. The medical electrical lead has a proximal end coupled to the ICD and a distal portion including one or more electrodes implanted substantially within an anterior mediastinum of a patient. The method further includes generating an electrical stimulation with the ICD in response to detecting the tachycardia and delivering the electrical stimulation to a heart of the patient via the one or more electrodes implanted substantially within the anterior mediastinum of the patient.

In another embodiment, an ICD system comprises an ICD implanted in a patient and an implantable medical electrical lead. The implantable medical lead includes an elongated lead body having a proximal end and a distal portion, a connector at the proximal end of the lead body configured to couple to the ICD, and a plurality of electrodes along the distal portion of the elongated lead body. The plurality of electrodes includes a defibrillation electrode and at least two sensing electrodes. The distal portion of the elongated lead body is implanted substantially within an anterior mediastinum of the patient. The ICD is configured to detect tachycardia using electrical signals sensed via the at least two sensing electrodes and to deliver one or more shocks to a heart of the patient via the defibrillation electrode in response to detecting tachycardia.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1A:
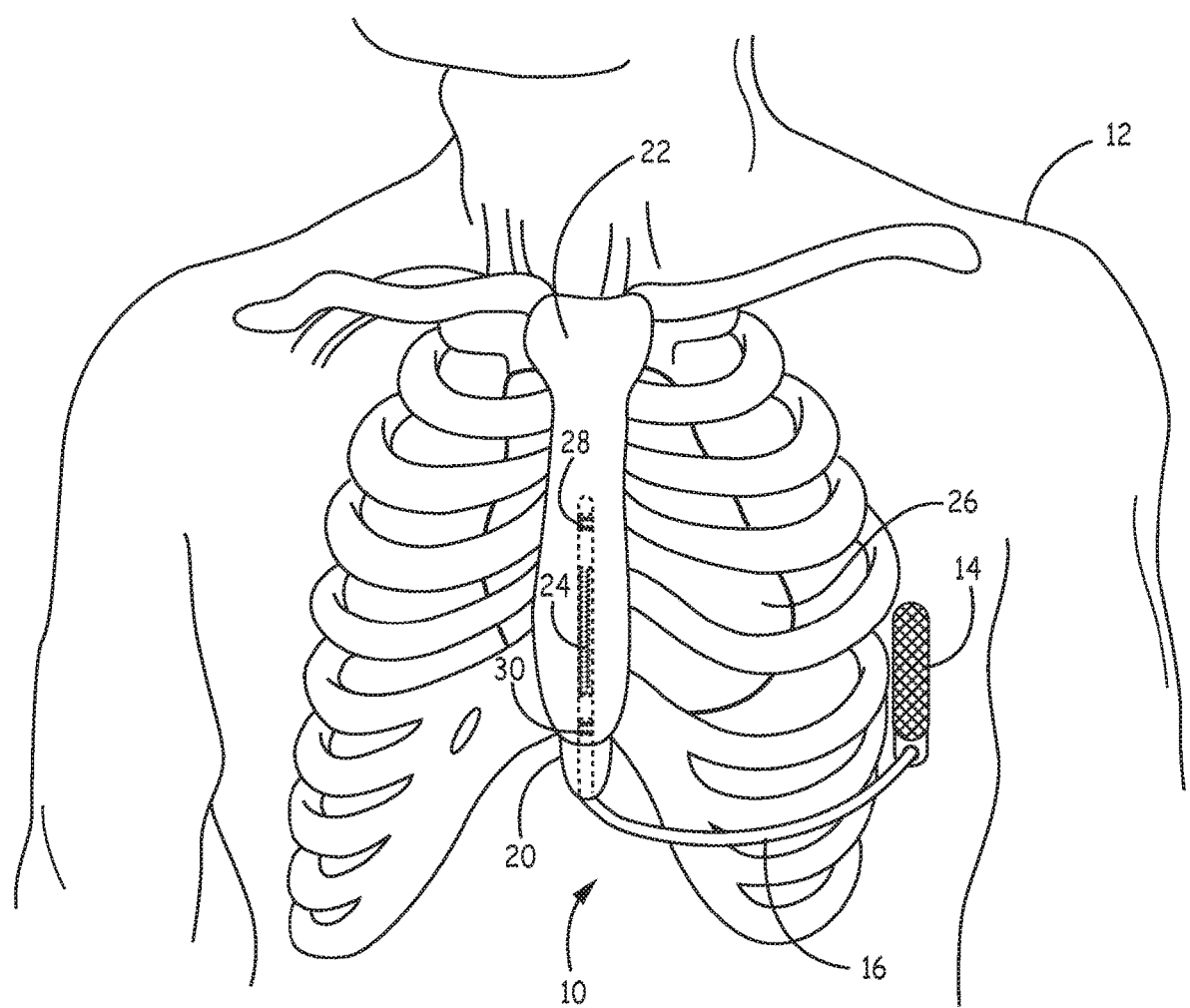
FIG. 1A is a front view of a patient implanted with a substernal ICD system.
Figure 1B:
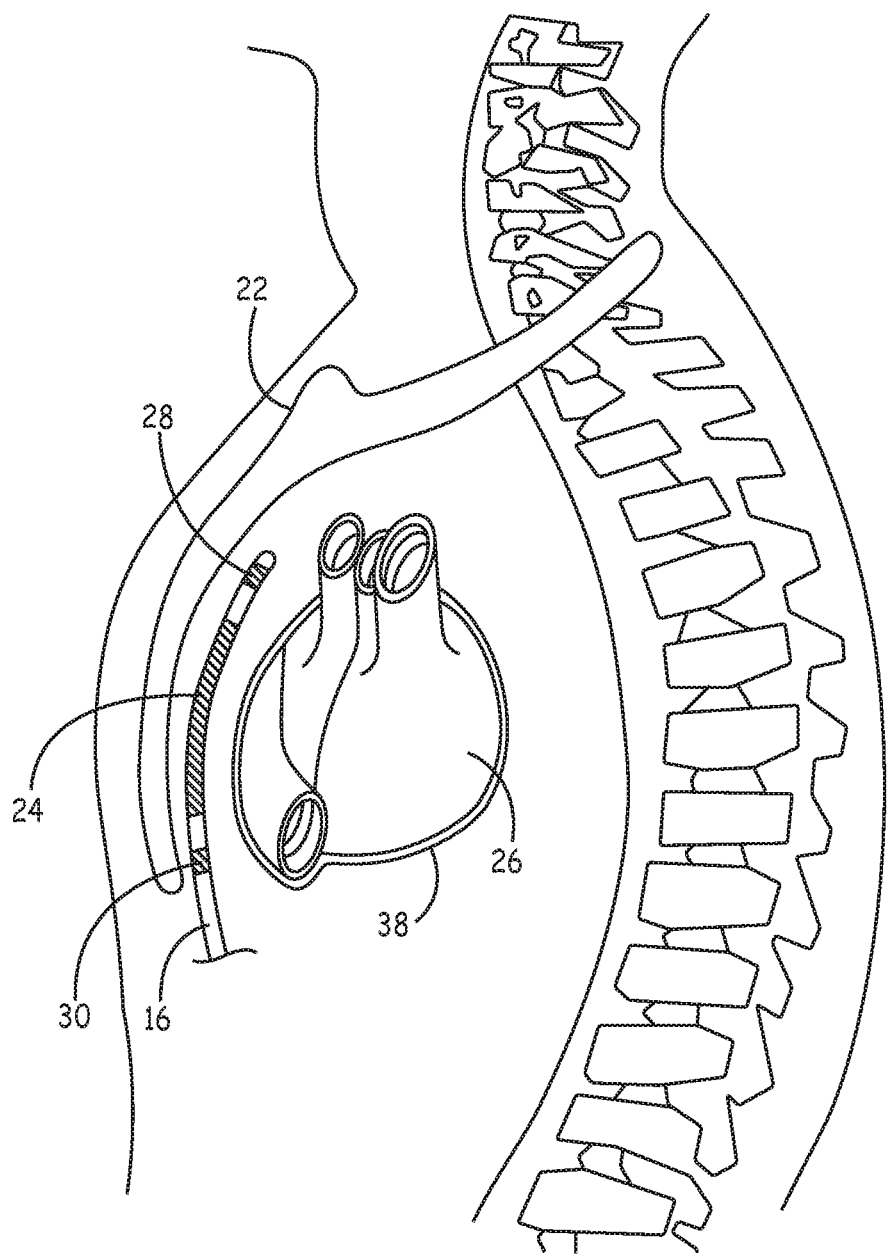
FIG. 1B is a side view of a patient implanted with a substernal ICD system.
Figure 1C:
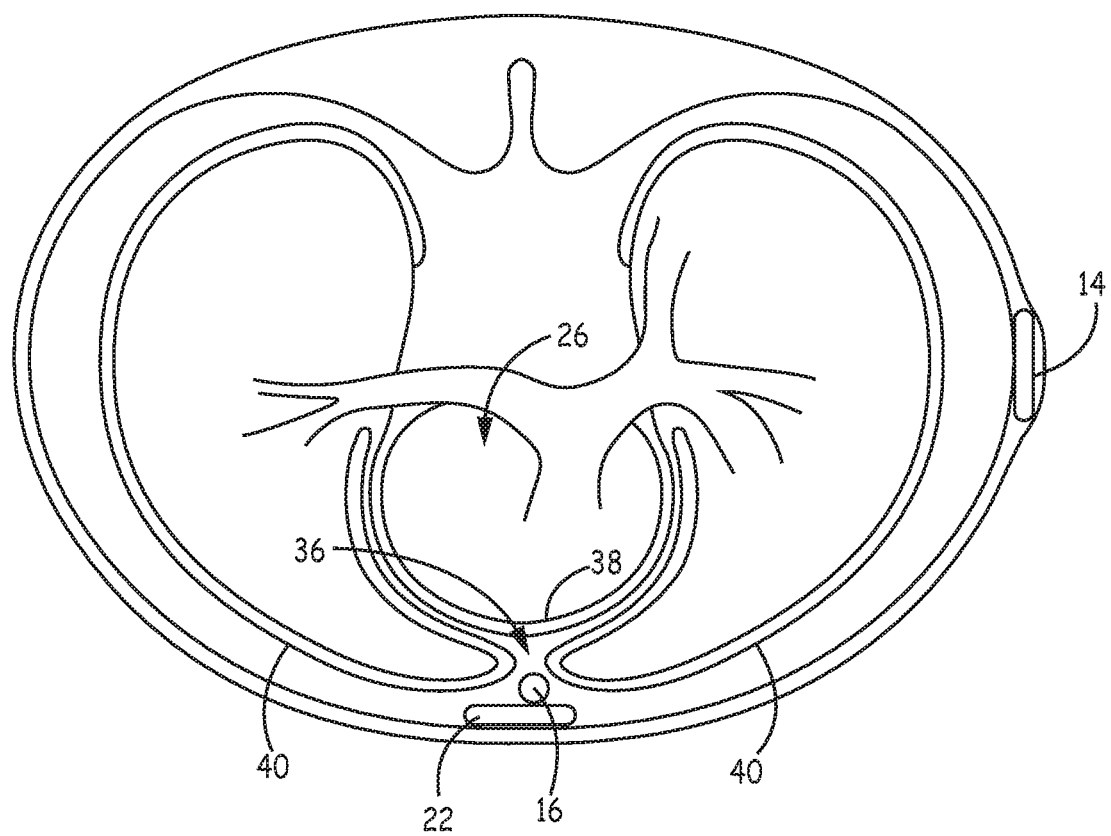
FIG. 1C is a transverse view of a patient implanted with a substernal ICD system.

FIGS. 1A-C are conceptual diagrams of an implantable cardioverter-defibrillation (ICD) system 10 implanted within a patient 12. FIG. 1A is a front view of ICD system 10 implanted within a patient 12. FIG. 1B is a side view of ICD system 10 implanted within a patient 12. FIG. 1C is a transverse view of ICD system 10 implanted within a patient 12. ICD system 10 includes an ICD 14 connected to a medical electrical lead 16. FIGS. 1A-C are described in the context of an ICD system capable of providing defibrillation and/or cardioversion shocks and, in some instances, pacing pulses. However, the techniques of this disclosure may also be used in the context of other implantable medical devices configured to provide electrical stimulation pulses to stimulate other portions of the body of patient 12.

ICD 14 may include a housing that forms a hermetic seal that protects components of ICD 14. The housing of ICD 14 may be formed of a conductive material, such as titanium, that may function as a housing electrode. ICD 14 may also include a connector assembly (also referred to as a connector block or header) that includes electrical feedthroughs through which electrical connections are made between lead 16 and electronic components included within the housing. As will be described in further detail herein, housing may house one or more processors, memories, transmitters, receivers, sensors, sensing circuitry, therapy circuitry, power sources and other appropriate components. The housing is configured to be implanted in a patient, such as patient 12. ICD 14 is implanted subcutaneously on the left midaxillary of patient 12. ICD 14 is on the left side of patient 12 above the ribcage. ICD 14 may, in some instances, be implanted between the left posterior axillary line and the left anterior axillary line of patient 12. ICD 14 may, however, be implanted at other subcutaneous locations on patient 12 as described later.

Lead 16 includes an elongated lead body having a proximal end that includes a connector (not shown) configured to be connected to ICD 14 and a distal portion that includes electrodes 24, 28, and 30. Lead 16 extends subcutaneously above the ribcage from ICD 14 toward a center of the torso of patient 12, e.g., toward xiphoid process 20 of patient 12. At a location near the center of the torso, lead 16 bends or turns and extends superior under/below sternum 22 within anterior mediastinum 36. Anterior mediastinum 36 may be viewed as being bounded laterally by pleurae 40, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 may be implanted substantially within the loose connective tissue and/or substernal musculature of anterior mediastinum 36. A lead implanted substantially within anterior mediastinum 36 will be referred to herein as a substernal lead. Also, electrical stimulation, such as pacing, cardioversion or defibrillation, provided by lead 16 implanted substantially within anterior mediastinum 36 will be referred to herein as substernal electrical stimulation, substernal pacing, substernal cardioversion, or substernal defibrillation.

The distal portion of lead 16 is described herein as being implanted substantially within anterior mediastinum 36. Thus, points along the distal portion of lead 16 may extend out of anterior mediastinum 36, but the majority of the distal portion is within anterior mediastinum 36. In other embodiments, the distal portion of lead 16 may be implanted in other non-vascular, extra-pericardial locations, including the gap, tissue, or other anatomical features around the perimeter of and adjacent to, but not attached to, the pericardium or other portion of heart 26 and not above sternum 22 or ribcage. As such, lead 16 may be implanted anywhere within the "substernal space" defined by the undersurface between the sternum and/or ribcage and the body cavity but not including the pericardium or other portion of heart 26. The substernal space may alternatively be referred to by the terms "retrosternal space" or "mediastinum" or "infrasternal" as is known to those skilled in the art and includes the anterior mediastinum 36. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, the distal portion of lead 16 may be implanted in the region around the outer surface of heart 26, but not attached to heart 26.

The distal portion of lead 16 may be implanted substantially within anterior mediastinum 36 such that electrodes 24, 28, and 30 are located near a ventricle of heart 26. For instance, lead 16 may be implanted within anterior mediastinum 36 such that electrode 24 is located over a cardiac silhouette of one or both ventricles as observed via an anterior-posterior (AP) fluoroscopic view of heart 26. In one example, lead 16 may be implanted such that a therapy vector from electrode 24 to a housing electrode of ICD 14 is substantially across the ventricles of heart 26. The therapy vector may be viewed as a line that extends from a point on electrode 24, e.g., center of electrode 24, to a point on the housing electrode of ICD 14, e.g., center of the housing electrode. However, lead 16 may be positioned at other locations as long as the therapy vector between electrode 24 and the housing electrode is capable of defibrillating heart 26.

In the example illustrated in FIGS. 1A-C, lead 16 is located substantially centered under sternum 22. In other instances, however, lead 16 may be implanted such that it is offset laterally from the center of sternum 22. In some instances, lead 16 may extend laterally enough such that all or a portion of lead 16 is underneath/below the ribcage in addition to or instead of sternum 22.

The elongated lead body of lead 16 contains one or more elongated electrical conductors (not illustrated) that extend within the lead body from the connector at the proximal lead end to electrodes 24, 28, and 30 located along the distal portion of lead 16. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. Other lead body designs may be used without departing from the scope of this disclosure. The lead body of lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 16 may engage with respective ones of electrodes 24, 28, and 30. In one example, each of electrodes 24, 28, and 30 is electrically coupled to a respective conductor within the lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, and 30 and transmit sensed electrical signals from one or more of electrodes 24, 28, and 30 to the sensing module within ICD 14.

Defibrillation electrode 24 is illustrated in FIG. 1 as being an elongated coil electrode. Defibrillation electrode 24 may vary in length depending on a number of variables. Defibrillation electrode 24 may, in one example, have a length between approximately 5-10 centimeters (cm). However, defibrillation electrode 24 may have a length less than 5 cm and greater than 10 cm in other embodiments. Another example, defibrillation electrode 24 may have a length between approximately 2-16 cm.

In other embodiments, however, defibrillation electrode 24 may be a flat ribbon electrode, paddle electrode, braided or woven electrode, mesh electrode, segmented electrode, directional electrode, patch electrode or other type of electrode besides an elongated coil electrode. In one example, defibrillation electrode 24 may be formed of a first segment and a second segment separated by a distance and having an electrode or a pair of electrodes (such as electrode 28 and/or 30 described below) located between the first and second defibrillation electrode segments. In one example, the segments may be coupled to the same conductor within the lead body such that the first and second segments function as a single defibrillation electrode. In other embodiments, defibrillation lead 16 may include more than one defibrillation electrode. For example, the first and second segments described above may be coupled to different conductors within the lead body such that the first and second segments function as separate defibrillation electrodes along the distal portion of lead 16. As another example, defibrillation lead 16 may include a second defibrillation electrode (e.g., second elongated coil electrode) near a proximal end of lead 16 or near a middle portion of lead 16.

Lead 16 also includes electrodes 28 and 30 located along the distal portion of lead 16. In the example illustrated in FIGS. 1A-C, electrode 28 and 30 are separated from one another by defibrillation electrode 24. In other examples, however, electrodes 28 and 30 may be both distal of defibrillation electrode 24 or both proximal of defibrillation electrode 24. In instances in which defibrillation electrode 24 is a segmented electrode with two defibrillation segments, electrodes 28 and 30 may be located between the two segments. Alternatively, one of electrodes 28 and 30 may be located between the two segments with the other electrode located proximal or distal to defibrillation electrode 24. Electrodes 28 and 30 may comprise ring electrodes, short coil electrodes, hemispherical electrodes, segmented electrodes, directional electrodes, or the like. Electrodes 28 and 30 of lead 16 may have substantially the same outer diameter as the lead body. In one example, electrodes 28 and 30 may have surface areas between 1.6-55 mm$^2$. Electrodes 28 and 30 may, in some instances, have relatively the same surface area or different surface areas. Depending on the configuration of lead 16, electrodes 28 and 30 may be spaced apart by the length of defibrillation electrode 24 plus some insulated length on each side of defibrillation electrode, e.g., approximately 2-16 cm. In other instances, such as when defibrillation 28 and 30 are between a segmented defibrillation electrode, the electrode spacing may be smaller, e.g., less than 2 cm or less the 1 cm. The example dimensions provided above are exemplary in nature and should not be considered limiting of the embodiments described herein. In other examples, lead 16 may include a single pace/sense electrode or more than two pace/sense electrodes.

In some instances, electrodes 28 and 30 of lead 16 may be shaped, oriented, designed or otherwise configured to reduce extracardiac stimulation. For example, electrodes 28 and 30 of lead 16 may be shaped, oriented, designed or otherwise configured to focus, direct or point electrodes 28 and 30 toward heart 26. In this manner, pacing pulses delivered via lead 16 are directed toward heart 26 and not outward toward skeletal muscle. For example, electrodes 28 and 30 of lead 16 may be partially coated or masked with a polymer (e.g., polyurethane) or another coating material (e.g., tantalum pentoxide) on one side or in different regions so as to direct the pacing signal toward heart 26 and not outward toward skeletal muscle.

ICD 14 may obtain sensed electrical signals corresponding with electrical activity of heart 26 via a combination of sensing vectors that include combinations of electrodes 28 and/or 30 and the housing electrode of ICD 14. For example, ICD 14 may obtain electrical signals sensed using a sensing vector between electrodes 28 and 30, obtain electrical signals sensed using a sensing vector between electrode 28 and the conductive housing electrode of ICD 14, obtain electrical signals sensed using a sensing vector between electrode 30 and the conductive housing electrode of ICD 14, or a combination thereof. In some instances, ICD 14 may even obtain sensed electrical signals using a sensing vector that includes defibrillation electrode 24.

ICD 14 analyzes the sensed electrical signals obtained from one or more of the sensing vectors of lead 16 to monitor for tachyarrhythmia, such as ventricular tachycardia or ventricular fibrillation. ICD 14 may analyze the heart rate and/or morphology of the sensed electrical signals to monitor for tachyarrhythmia in accordance with any of a number of techniques known in the art. One example technique for detecting tachyarrhythmia is described in U.S. Pat. No. 7,761,150 to Ghanem et al., entitled "METHOD AND APPARATUS FOR DETECTING ARRHYTHMIAS IN A MEDICAL DEVICE." The entire content of the tachyarrhythmia detection algorithm described in Ghanem et al. are incorporated by reference herein in their entirety. The sensed electrical signals sensed using substernal lead 16 may be analyzed in the same way as the subcutaneously sensed electrical signals of Ghanem et al.

ICD 14 generates and delivers substernal electrical stimulation therapy in response to detecting tachycardia (e.g., VT or VF). In response to detecting the tachycardia, ICD 14 may deliver one or more sequences of ATP via the one or more therapy vectors of lead 16, e.g., unipolar therapy vector, bipolar pacing vector or multipolar pacing vector (e.g., by electrodes 28 and 30 together as an anode or cathode) in an attempt to terminate the tachycardia without delivering a defibrillation shock. For example, ICD 14 may deliver ATP using a bipolar therapy vector between electrodes 28 and 30. In another example, ICD 14 may deliver ATP using a unipolar therapy vector (e.g., between electrode 28 and the conductive housing electrode of ICD 14 or between electrode 30 and the conductive housing electrode of ICD 14). In a further example, ICD 14 may deliver ATP via a therapy vector in which electrodes 28 and 30 together form the cathode (or anode) of the therapy vector and the housing electrode of ICD 14 functions as the anode (or cathode) of the therapy vector. In yet another example, ICD 14 may deliver ATP using a therapy vector that include defibrillation electrode 24.

If the one or more sequences of ATP are not successful or it is determined that ATP is not desired (e.g., in the case of VF), ICD 14 may deliver one or more cardioversion or defibrillation shocks via defibrillation electrode 24 of lead 16. ICD 14 may generate and deliver electrical stimulation therapy other than ATP and cardioversion or defibrillation shocks, including post-shock pacing, bradycardia pacing, or other electrical stimulation. In this manner, ICD 14 may deliver substernal electrical stimulation that have reduced energies as compared to subcutaneous ICD systems yet not require a lead that enters the vasculature, is implanted within heart 26 or attached to heart 26.

Lead 16 may further include one or more anchoring mechanisms that are positioned on the distal end, along the length of the lead body, or near the incision/entry site. The anchoring mechanisms may affix lead 16 to reduce movement of lead 16 from its desired substernal location. For example, the lead 16 may be anchored at one or more locations situated between the distal end and a point along the length of the portion of the lead body extending superior from the xiphoid process under sternum 22. The one or more anchoring mechanism(s) may either engage fascia, muscle or tissue of patient 12 or may simply be wedged therein to affix the lead to prevent excessive motion or dislodgment. The anchoring mechanisms may be integrated into the lead body. In alternative embodiments, the anchoring mechanisms may be discrete elements formed in line with the lead body, such as a helix, rigid tines, prongs, barbs, clips, screws, and/or other projecting elements or flanges, disks, pliant tines, flaps, porous structures such as a mesh-like element that facilitate tissue growth for engagement, bioadhesive surfaces, and/or any other non-piercing elements. In addition or alternatively, the lead may be anchored through a suture (e.g., using an anchoring sleeve) that fixedly-secures the lead to the patient's musculature, tissue or bone at the xiphoid entry site. In some embodiments, the suture may be sewn through pre-formed suture holes to the patient.

The examples illustrated in FIGS. 1A-C are exemplary in nature and should not be considered limiting of the techniques described in this disclosure. In other examples, ICD 14 and lead 16 may be implanted at other locations. For example, ICD 14 may be implanted in a subcutaneous pocket in the right pectoral region. In this example, defibrillation lead 16 may extend subcutaneously from the device toward the manubrium of sternum 22 and bend or turn and extend inferior from the manubrium underneath/below the sternum to the desired location. In yet another example, ICD 14 may be placed abdominally.

In the example illustrated in FIG. 1, system 10 is an ICD system that provides cardioversion/defibrillation and pacing therapy. However, these techniques may be applicable to other cardiac systems, including cardiac resynchronization therapy defibrillator (CRT-D) systems or other cardiac stimulation therapies, or combinations thereof. For example, ICD 14 may be configured to provide electrical stimulation pulses to stimulate nerves, skeletal muscles, diaphragmatic muscles, e.g., for various neuro-cardiac applications and/or for apnea or respiration therapy. As another example, lead 16 may be placed further superior such that the defibrillation electrode 24 is placed substantially over the atrium of heart 26. In this case, system 10 may be used to provide a shock or pulse to terminate atrial fibrillation (AF).

In addition, it should be noted that system 10 may not be limited to treatment of a human patient. In alternative examples, system 10 may be implemented in non-human patients, e.g., primates, canines, equines, pigs, ovines, bovines, and felines. These other animals may undergo clinical or research therapies that may benefit from the subject matter of this disclosure.

Figure 2:
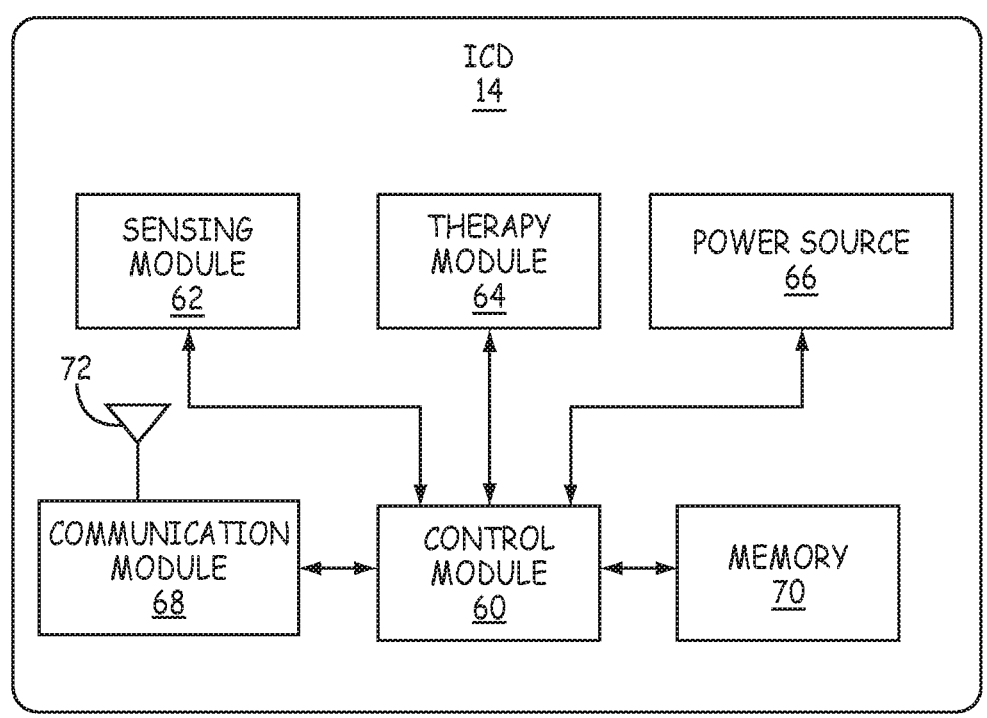
FIG. 2 is a functional block diagram of an example configuration of electronic components of an example ICD.

FIG. 2 is a functional block diagram of an example configuration of electronic components of an example ICD 14. ICD 14 includes a control module 60, sensing module 62, therapy module 64, communication module 68, and memory 70. The electronic components may receive power from a power source 66, which may be a rechargeable or non-rechargeable battery. In other embodiments, ICD 14 may include more or fewer electronic components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Sensing module 62 is electrically coupled to some or all of electrodes 24, 28, and 30 via the conductors of lead 16 and one or more electrical feedthroughs, or to the housing electrode via conductors internal to the housing of ICD 14. Sensing module 62 is configured to obtain signals sensed via one or more combinations of electrodes 24, 28, and 30 and the housing electrode of ICD 14 and process the obtained signals.

The components of sensing module 62 may be analog components, digital components or a combination thereof. Sensing module 62 may, for example, include one or more sense amplifiers, filters, rectifiers, threshold detectors, analog-to-digital converters (ADCs) or the like. Sensing module 62 may convert the sensed signals to digital form and provide the digital signals to control module 60 for processing or analysis. For example, sensing module 62 may amplify signals from the sensing electrodes and convert the amplified signals to multi-bit digital signals by an ADC. Sensing module 62 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 60.

Control module 60 may process the signals from sensing module 62 to monitor electrical activity of heart 26 of patient 12. Control module 60 may store signals obtained by sensing module 62 as well as any generated EGM waveforms, marker channel data or other data derived based on the sensed signals in memory 70. Control module 60 may analyze the EGM waveforms and/or marker channel data to detect cardiac events (e.g., tachycardia). In response to detecting the cardiac event, control module 60 may control therapy module 64 to deliver the desired therapy to treat the cardiac event, e.g., defibrillation shock, cardioversion shock, ATP, post shock pacing, bradycardia pacing.

Therapy module 64 is configured to generate and deliver electrical stimulation therapy to heart 26. Therapy module 64 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy module 64 may include a first set of components configured to provide pacing therapy and a second set of components configured to provide defibrillation therapy. In other instances, therapy module 64 may utilize the same set of components to provide both pacing and defibrillation therapy. In still other instances, therapy module 64 may share some of the defibrillation and pacing therapy components while using other components solely for defibrillation or pacing.

Control module 60 may control therapy module 64 to deliver the generated therapy to heart 26 via one or more combinations of electrodes 24, 28, and 30 and the housing electrode of ICD 14 according to one or more therapy programs, which may be stored in memory 70. Control module 60 controls therapy module 64 to generate electrical stimulation therapy with the amplitudes, pulse widths, timing, frequencies, electrode combinations or electrode configurations specified by a selected therapy program.

In the case of pacing therapy, e.g., ATP, post-shock pacing, and/or bradycardia pacing provided via electrodes 28 and/or 30 of lead 16, control module 60 controls therapy module 64 may generate and deliver pacing pulses with any of a number of shapes, amplitudes, pulse widths, or other characteristic to capture heart 26. For example, the pacing pulses may be monophasic, biphasic, or multi-phasic (e.g., more than two phases). The pacing thresholds of heart 26 when delivering pacing pulses from the substernal space, e.g., from electrodes 28 and/or 30 substantially within anterior mediastinum 36, may depend upon a number of factors, including location, type, size, orientation, and/or spacing of electrodes 28 and 30, location of ICD 14 relative to electrodes 28 and 30, physical abnormalities of heart 26 (e.g., pericardial adhesions or myocardial infarctions), or other factor(s).

The increased distance from electrodes 28 and 30 of lead 16 to the heart tissue may result in heart 26 having increased pacing thresholds compared to transvenous pacing thresholds. To this end, therapy module 64 may be configured to generate and deliver pacing pulses having larger amplitudes and/or pulse widths than conventionally required to obtain capture via leads implanted within the heart (e.g., transvenous leads) or leads attached directly to heart 26. In one example, therapy module 64 may generate and deliver pacing pulses having amplitudes of less than or equal to 8 volts and pulse widths between 0.5-3.0 milliseconds. In another example, therapy module 64 may generate and deliver pacing pluses having amplitudes of between 5 and 10 volts and pulse widths between approximately 3.0 milliseconds and 10.0 milliseconds. In another example, therapy module 64 may generate and deliver pacing pluses having pulse widths between approximately 2.0 milliseconds and 8.0 milliseconds. In a further example, therapy module 64 may generate and deliver pacing pluses having pulse widths between approximately 0.5 milliseconds and 20.0 milliseconds. In another example, therapy module 64 may generate and deliver pacing pluses having pulse widths between approximately 1.5 milliseconds and 20.0 milliseconds.

Pacing pulses having longer pulse durations than conventional transvenous pacing pulses may result in lower energy consumption. As such, therapy module 64 may be configured to generate and deliver pacing pulses having pulse widths or durations of greater than two (2) milliseconds. In another example, therapy module 64 may be configured to generate and deliver pacing pulses having pulse widths or durations of between greater than two (2) milliseconds and less than or equal to three (3) milliseconds. In another example, therapy module 64 may be configured to generate and deliver pacing pulses having pulse widths or durations of greater than or equal to three (3) milliseconds. In another example, therapy module 64 may be configured to generate and deliver pacing pulses having pulse widths or durations of greater than or equal to five (5) milliseconds. In another example, therapy module 64 may be configured to generate and deliver pacing pulses having pulse widths or durations of greater than or equal to ten (10) milliseconds. In a further example, therapy module 64 may be configured to generate and deliver pacing pulses having pulse widths between approximately 3-10 milliseconds. In a further example, therapy module 64 may be configured to generate and deliver pacing pulses having pulse widths or durations of greater than or equal to fifteen (15) milliseconds. In yet another example, therapy module 64 may be configured to generate and deliver pacing pulses having pulse widths or durations of greater than or equal to twenty (20) milliseconds.

Depending on the pulse widths, ICD 14 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths as illustrated in the experimental results. Reducing the amplitude of pacing pulses delivered by ICD 14 reduces the likelihood of extra-cardiac stimulation and lower consumed energy of power source 66. Some experimental results are provided later illustrating some example combinations of pacing amplitudes and widths.

In the case of cardioversion or defibrillation therapy, e.g., cardioversion or defibrillation shocks provided by defibrillation electrode 24 of lead 16, control module 60 controls therapy module 64 to generate cardioversion or defibrillation shocks having any of a number of waveform properties, including leading-edge voltage, tilt, delivered energy, pulse phases, and the like. Therapy module 64 may, for instance, generate monophasic, biphasic or multiphasic waveforms. Additionally, therapy module 64 may generate cardioversion or defibrillation waveforms having different amounts of energy. As with pacing, delivering cardioversion or defibrillation shocks from the substernal space, e.g., from electrode 24 substantially within anterior mediastinum 36, may reduce the amount of energy that needs to be delivered to defibrillate heart 26. As one example, therapy module 64 may generate and deliver cardioversion or defibrillation shocks having energies of less than 80 J. As another example, therapy module 64 may generate and deliver cardioversion or defibrillation shocks having energies of less than 65 J. As one example, therapy module 64 may generate and deliver cardioversion or defibrillation shocks having energies of less than 60 Joules (J). In some instances, therapy module 64 may generate and deliver cardioversion or defibrillation shocks having energies between 40-50 J. In other instances, therapy module 64 may generate and deliver cardioversion or defibrillation shocks having energies between 35-60 J. In still other instances, therapy module 64 may generate and deliver cardioversion or defibrillation shocks having energies less than 35 J. Subcutaneous ICD systems on the other hand generate and deliver cardioversion or defibrillation shocks having an energy around 80 J. Placing defibrillation lead 16 within the substernal space, e.g., with the distal portion substantially within anterior mediastinum 36, may result in reduced energy consumption and, in turn, smaller devices and/or devices having increased longevity.

Therapy module 64 may also generate defibrillation waveforms having different tilts. In the case of a biphasic defibrillation waveform, therapy module 64 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide substernal defibrillation via defibrillation electrode 24.

Communication module 68 includes any suitable hardware, firmware, software or any combination thereof for communicating with another device, such as a clinician programmer, a patient monitoring device, or the like. For example, communication module 68 may include appropriate modulation, demodulation, frequency conversion, filtering, and amplifier components for transmission and reception of data with the aid of antenna 72. Antenna 72 may be located within connector block of ICD 14 or within housing ICD 14.

The various modules of ICD 14 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 70 may include computer-readable instructions that, when executed by control module 60 or other component of ICD 14, cause one or more components of ICD 14 to perform various functions attributed to those components in this disclosure. Memory 70 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 3:
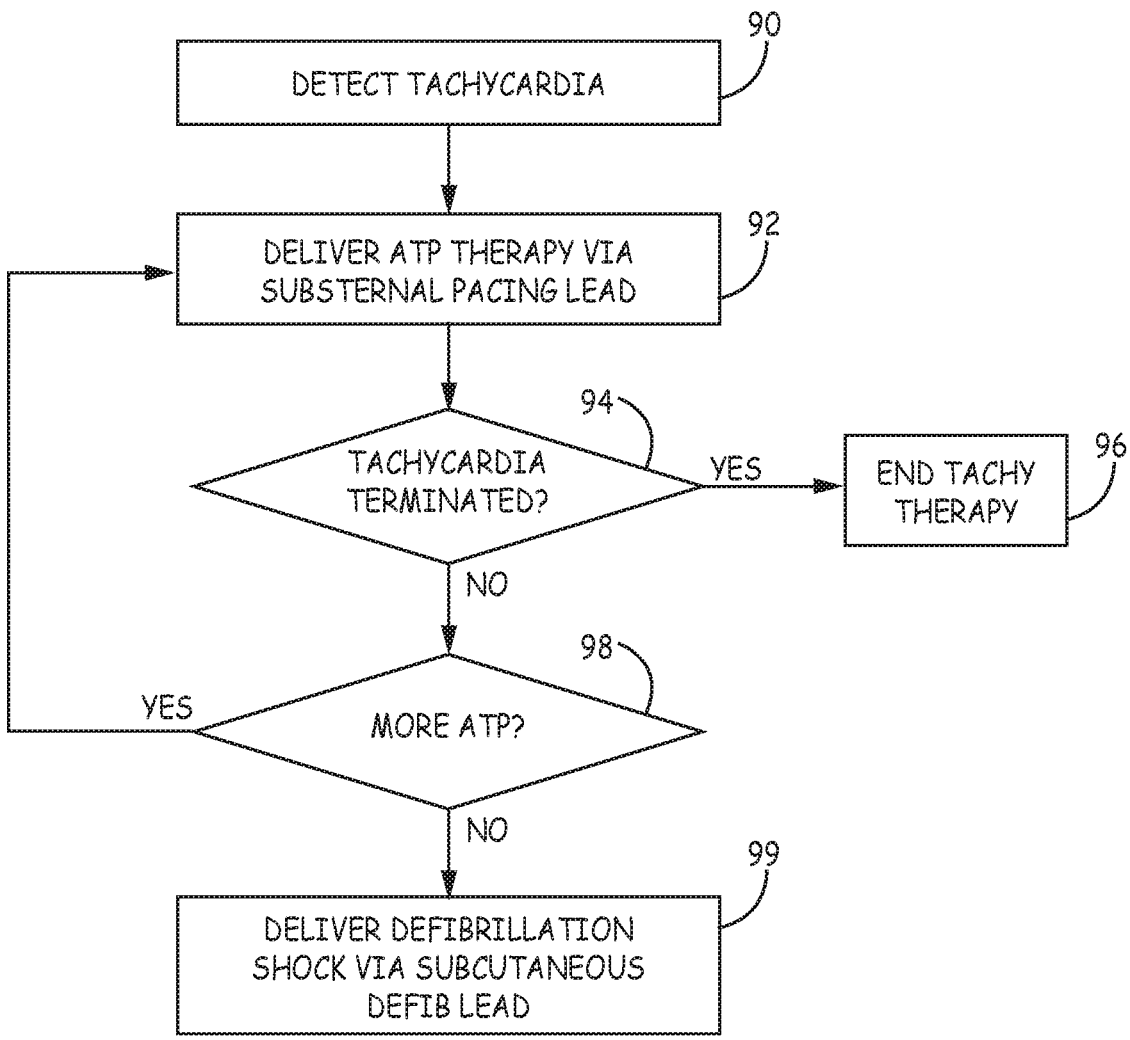
FIG. 3 is a flow diagram illustrating example operation of a substernal ICD system.

FIG. 3 is a flow diagram illustrating example operation of a substernal ICD system, such as ICD system 10 of FIGS. 1A-1C. Initially, ICD 14 analyzes sensed electrical signals from one or more sensing vectors formed using electrodes 28 and/or 30 of lead 16 to detect tachycardia, such as ventricular tachycardia or ventricular fibrillation (90).

ICD 14 delivers a sequence of ATP pacing pulses via a therapy vector that includes at least one of electrodes 28 or 30 of lead 16 having a distal portion implanted substantially within anterior mediastinum 36 (92). ICD 14 may deliver the sequence of ATP pacing pulses to heart 26 via a pacing vector that includes any combination of one or both of electrodes 28 and 30 and a housing electrode of ICD 14, e.g., via a bipolar or unipolar pacing vector. As described above, the pacing pulses provided by ICD 14 may have longer pulse widths than conventional pacing pulses. For example, ICD 14 may be configured to deliver pacing pulses having pulse widths of greater than two milliseconds. In other instances, ICD 14 may be configured to deliver pacing pulses having pulse widths of between three and ten milliseconds. Other ranges of pulse widths, as well as pacing amplitudes, rates, number of pulses, and the like and various combinations of characteristics are described in further detail herein.

In some instances, ICD 14 may be configured to only deliver ATP to particular types of tachycardia. ICD 14 may, for example, distinguish between VT and VF using any of a number of techniques known in the art and only provide ATP in instances in which the tachycardia is VT. If the tachycardia is VF, the ICD 14 may be configured to not provide ATP and instead only deliver defibrillation or cardioversion therapy.

After delivery of the sequence of ATP pacing pulses, ICD 14 determines whether the tachycardia is terminated (94). ICD 14 may, for example, analyze the most recent sensed activity of the heart to determine if the sequence of ATP pacing pulses terminated the tachycardia. When ICD 14 determines that the tachycardia has terminated ("YES" branch of block 94), ICD 14 ends the tachycardia therapy and returns to analyzing sensed electrical signals (96).

When ICD 14 determines that the tachycardia has not terminated ("NO" branch of block 94), ICD 14 determines whether additional sequences of ATP pacing pulses will be provided (98). ICD 14 may, for example, be configured to deliver ATP therapy that consists of two or more sequences of ATP pacing pulses. When ICD 14 determines that additional sequences of ATP pacing pulses will be provided ("YES" branch of block 98), ICD 14 delivers a second sequence of ATP pacing pulses via at least one of electrodes 28 or 30 of lead 16 having a distal portion implanted substantially within anterior mediastinum 36 (92). The second sequence of pacing pulses may be the same as the first sequence. Alternatively, the second sequence of pacing pulses may be different than the first sequence. For example, the ATP pulses of the first and second sequences of pulses may have one or more different characteristics including, but not limited to, different pacing amplitudes, pulse widths, rates, therapy vectors, and/or variation among pacing pulses.

When ICD 14 determines that no additional sequences of ATP pacing pulses will be provided ("NO" branch of block 98), ICD 14 delivers a defibrillation or cardioversion shock via a therapy vector that includes defibrillation electrode 24 of lead 16 implanted at least partially within anterior mediastinum 36 (99).

Experiments

Three acute procedures were performed using pigs, with the animals in a dorsal recumbency. An incision was made near the xiphoid process and a Model 4194 lead was delivered to the substernal/retrosternal space using a 6996T tunneling tool and sheath. An active can emulator (ACE) was placed in a subcutaneous pocket on either the right chest (first acute experiment) or the left midaxillary (second and third acute experiments). Various pacing configurations were tried and different pieces of equipment were used as the source of stimulation. Multiple pulse widths were used in delivering the pacing pulse. Across experiments, several different substernal/retrosternal lead electrode locations were utilized.

In the second and third experiments the impact of lead location on electrical performance was investigated by moving the lead to several locations under the sternum and collecting data to generate strength-duration curves at each location.

In all three acute experiments, the substernal/retrosternal lead was placed and electrical data collected. The lead was moved intentionally many times across experiments to better understand the location best suited to capturing the heart at low pacing thresholds, with different locations and parameters tried until pacing capability was gained and lost. A range of thresholds based on location and pacing configuration was recorded. For this reason, the lowest threshold result for each acute experiment is reported, as are strength-duration curves showing the range of pacing values obtained from suitable pacing locations. In all cases, it was determined that positioning the substernal/retrosternal pacing electrode approximately over the ventricle of the cardiac silhouette provided best results.

Experiment 1

In the first acute study, a Medtronic Attain bipolar OTW 4194 lead was implanted substernally/retrosternally, and two active can emulators were positioned, one in the right dorsal lateral region (ACE1) and one on the right midaxillary (ACE2). The 4194 lead was placed directly below the sternum, in the mediastinum, with the lead tip and body running parallel to the length of the sternum. Various pacing configurations were tried and electrical data collected.

The smallest threshold observed was 0.8 volts, obtained when pacing from the tip of the substernal/retrosternal 4194 lead to ACE1 (10 ms pulse width and Frederick Heir instrument as the source of stimulation). It was possible to capture using a smaller pulse width, though threshold increased as the pulse width shortened (1.5V at 2 ms in this same configuration with a bp isolater, made by FHC product #74-65-7, referred to herein as "Frederick Heir Stimulator." Many additional low thresholds (1-2 volts) were obtained with different pacing configurations and pulse durations.

Figure 4:
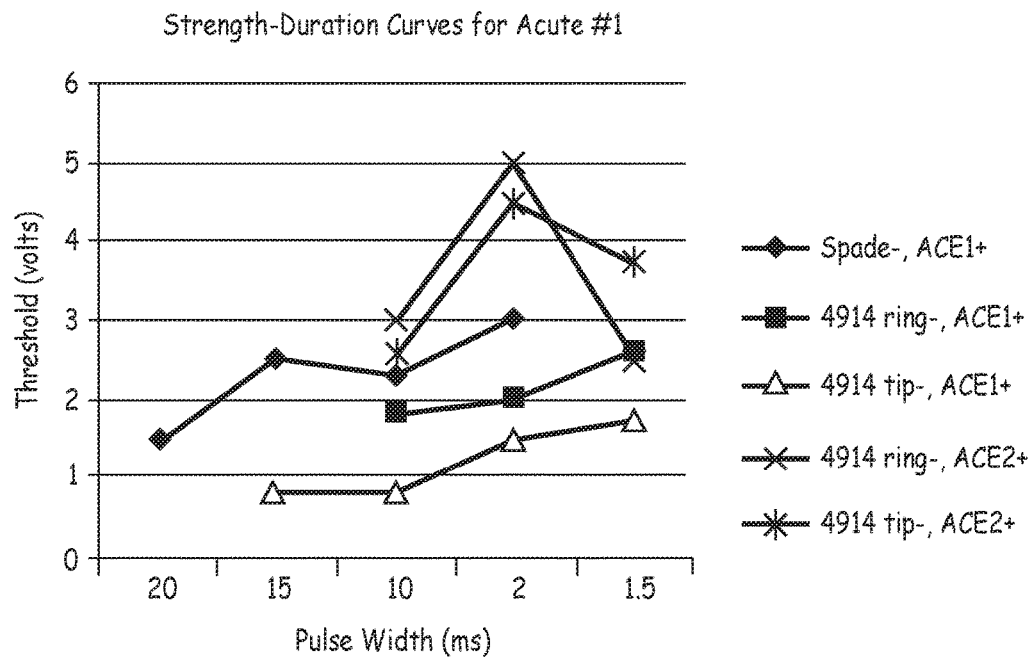
FIG. 4 is a graph illustrating strength-duration curves showing the capture thresholds obtained at various pulse widths during a first acute study.

FIG. 4 illustrates a strength-duration curve showing the capture thresholds obtained at various pulse widths during the first acute study. Note that all configurations paced from either the tip or the ring of the substernally/retrosternally implanted 4194 lead (−) to one of the two active can emulators (+). In one instance, a large spade electrode (instead of a Model 4194 lead) was used as the substernal/retrosternal electrode, as noted in the legend of FIG. 4.

As shown, several pacing configurations and parameters were tried. Across the configurations reported in the graph above, threshold values ranged from 0.8 volts to 5.0 volts, with threshold generally increasing as pulse width was shortened. In a few instances, the threshold at 1.5 ms pulse width was smaller than the threshold at 2.0 ms. It should be noted that the threshold value obtained at 1.5 ms was always recorded using the Medtronic 2290 analyzer as the stimulation source, whereas all other threshold measurements for the first acute experiment (at pulse widths of 2, 10, 15 and 20 ms) were obtained using a Frederick Heir instrument as the source of stimulation. Differences in these two instruments may account for the difference in threshold values at similar pulse widths (1.5 ms and 2 ms).

In general, the first acute experiment demonstrated the feasibility of substernal/retrosternal pacing by producing small capture thresholds (average=2.5±1.2 volts), using several different pacing configurations and parameters.

Experiment 2

A second acute experiment was conducted. In the second acute, however, the animal presented with pericardial adhesions to the sternum. Because of the pericardial adhesion, the ventricular surface of the cardiac silhouette was rotated away from the sternum—an anatomical difference that may have resulted in higher thresholds throughout this experiment.

As in the previous acute experiment, a Model 4194 lead was placed under the sternum. An active can emulator was placed on the left midaxillary. The tip to ring section of the 4194 was positioned over the cardiac silhouette of the ventricle, as observed by fluoroscopy, and this position is notated "Position A" on the strength-duration graph illustrated in FIG. 5. The lead eventually migrated a very short distance closer to the xiphoid process during stimulation (still under the sternum) to reach "Position B," and additional electrical measurements were obtained successfully from this position as well.

The smallest threshold observed in the second acute experiment was 7V, obtained when pacing from the substernal/retrosternal 4194 ring electrode (−) to an ACE (+) on the left midaxillary in the first lead position (5 ms, 15 ms and 20 ms pulse widths, Frederick Heir stimulator). Additionally, thresholds of 8 and 9 volts were obtained with the lead in the second anatomical position, both from 4194 tip to ACE (unipolar) and 4194 tip to ring (bipolar) configurations at multiple pulse widths. The two lines that appear to run off the chart were instances of no capture.

Figure 5:
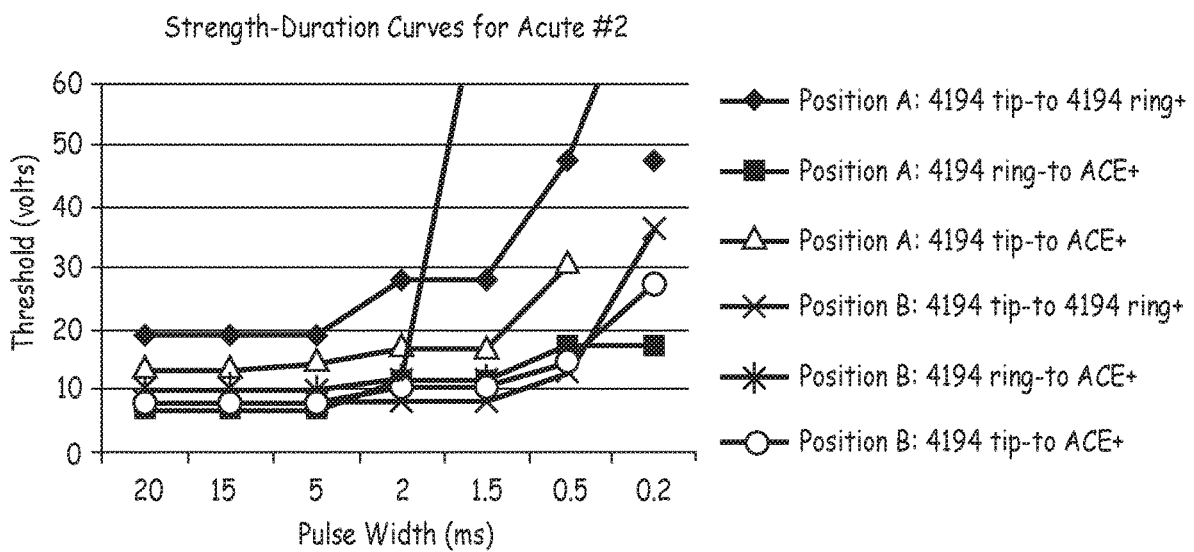
FIG. 5 is a graph illustrating strength-duration curves showing the capture thresholds obtained at various pulse widths during a second acute study.

All of the electrical values reported in FIG. 5 were collected with the Frederick Heir instrument as the stimulation source. Extracardiac stimulation was observed with many of the electrical measurements obtained in a unipolar pacing configuration. No obvious extracardiac stimulation was observed when pacing in a bipolar configuration (4194 tip to ring), though a low level of stimulation could be felt with a hand on the animal's chest.

Experiment 3

A third and final acute experiment was conducted demonstrating the feasibility of substernal/retrosternal pacing. As in the previous two acute experiments, a 4194 lead was placed under the sternum. An active can emulator was placed on the left midaxillary. In this experiment, the substernal/retrosternal 4194 lead was intentionally positioned so that the lead tip was initially near the second rib, far above the cardiac silhouette of the ventricle. The lead tip was then pulled back (toward the xiphoid process) one rib space at a time, collecting electrical data at each position. As in previous experiments, low capture thresholds were obtained when the pacing electrodes were approximately positioned over the ventricular surface of the cardiac silhouette, as observed via fluoroscopy. When the lead tip was not over the ventricular surface of the cardiac silhouette, "no capture" was often the result.

As in previous experiments, pacing was performed from either the tip or the ring of the substernal/retrosternal 4194 lead (−) to the ACE (+) on the left midaxillary. However, in this acute experiment, a subcutaneous ICD lead was also positioned in its subcutaneous arrangement (as illustrated and described in FIGS. 1A-C). In some instances, the pacing configuration was from either the tip or the ring of the substernal/retrosternal 4194 lead (−) to either the ring or the coil of the subcutaneous ICD lead (+), so that the ICD lead and not the ACE was the indifferent electrode.

The smallest threshold observed across the experiment was 0.8V, obtained when pacing from the substernal/retrosternal 4194 tip electrode (−) to an ACE (+) on the left midaxillary when the lead was positioned such that the lead tip electrode was approximately under the sixth rib (20 ms pulse width and Frederick Heir stimulator). Many additional low thresholds were obtained with different pacing configurations, shorter pulse durations and different lead positions, again demonstrating the feasibility of sub sternal/retrosternal pacing. Obvious extracardiac stimulation generally was not observed with lower threshold measurements (at longer pulse durations) but was observed at higher thresholds.

Figure 6:
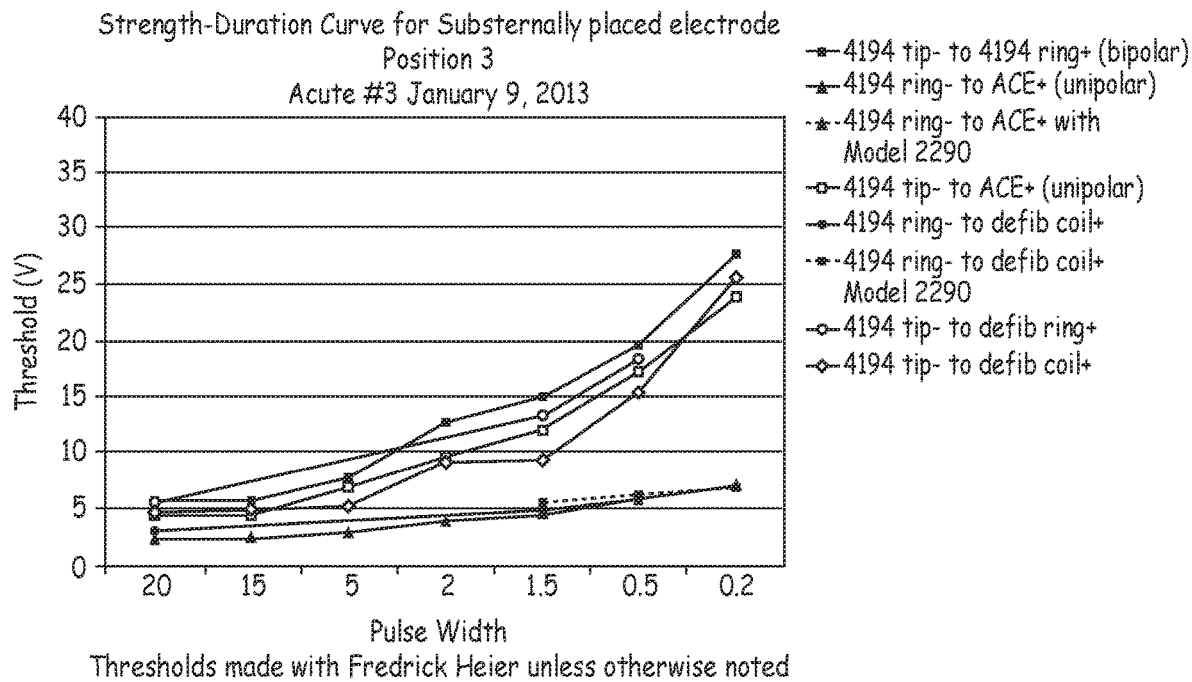
FIG. 6 is a graph illustrating strength-duration curves of electrical data from a third acute experiment with the lead positioned under the sternum at a first location.
Figure 7:
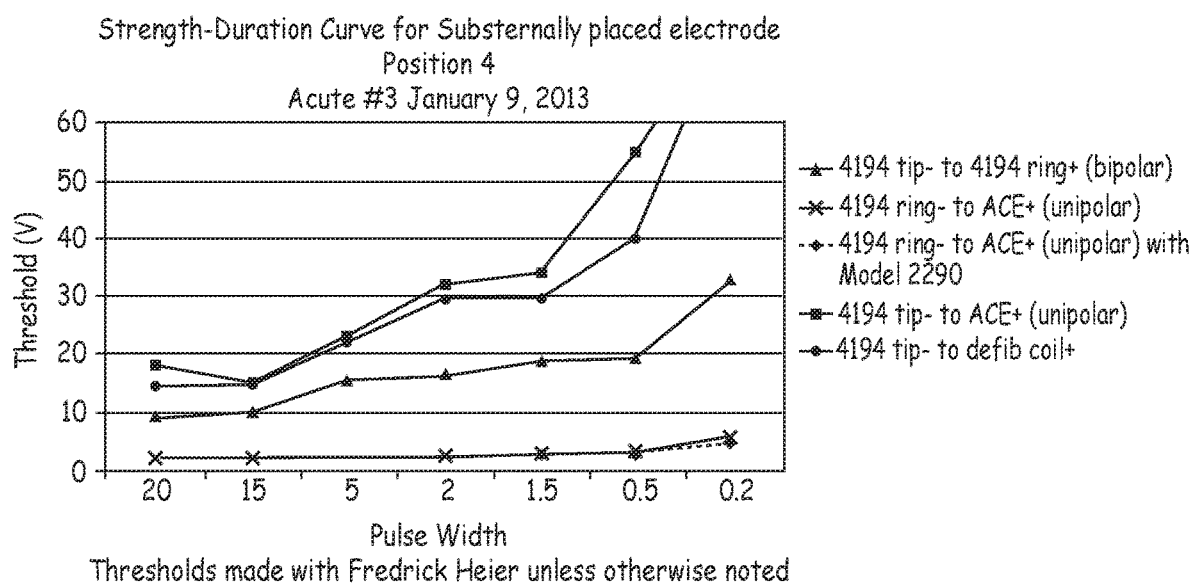
FIG. 7 is a graph illustrating strength-duration curves of electrical data from the third acute experiment with the lead positioned under the sternum at a second location.

The strength duration curves for lead positions 3-5 are presented in FIGS. 5-7, with individual graphs for each location due to the breadth of electrical data collected. Measurements made with the 2290 analyzer as the source of stimulation are noted. Other electrical measurements were made with the Frederick Heir instrument as the stimulation source.

FIG. 6 illustrates the strength-duration curve of electrical data from the third acute experiment when the 4194 lead tip was positioned under the sternum near the location of the $4^{th}$ rib. Several therapy vectors resulted in low pacing thresholds, generally when pulse widths were quite long. At shorter pulse widths, threshold increased.

FIG. 7 illustrates the strength-duration curve of electrical data from the third acute experiment when the 4194 lead tip was positioned under the sternum near the location of the $5^{th}$ rib. The two lines that appear to run off the chart at 0.2 ms were instances of no capture. FIG. 7 demonstrates the position dependence of the substernal/retrosternal lead. Thresholds were higher overall in this anatomical location (the lead tip near the $5^{th}$ rib), though capture was still possible and in the 4194 ring (−) to ACE (+) configuration, moderately low (2 volts at 20 ms). There generally was no significant extracardiac stimulation observed except with pulse widths of 0.2 ms and 0.5 ms in the 4194 tip (−) to ACE (+) configuration and in the unipolar configuration going from the 4194 tip (−) to the coil of the subcutaneous ICD lead at pulse widths of 1.5 ms and shorter, all of which resulted in the highest recorded threshold readings in this lead position.

Figure 8:
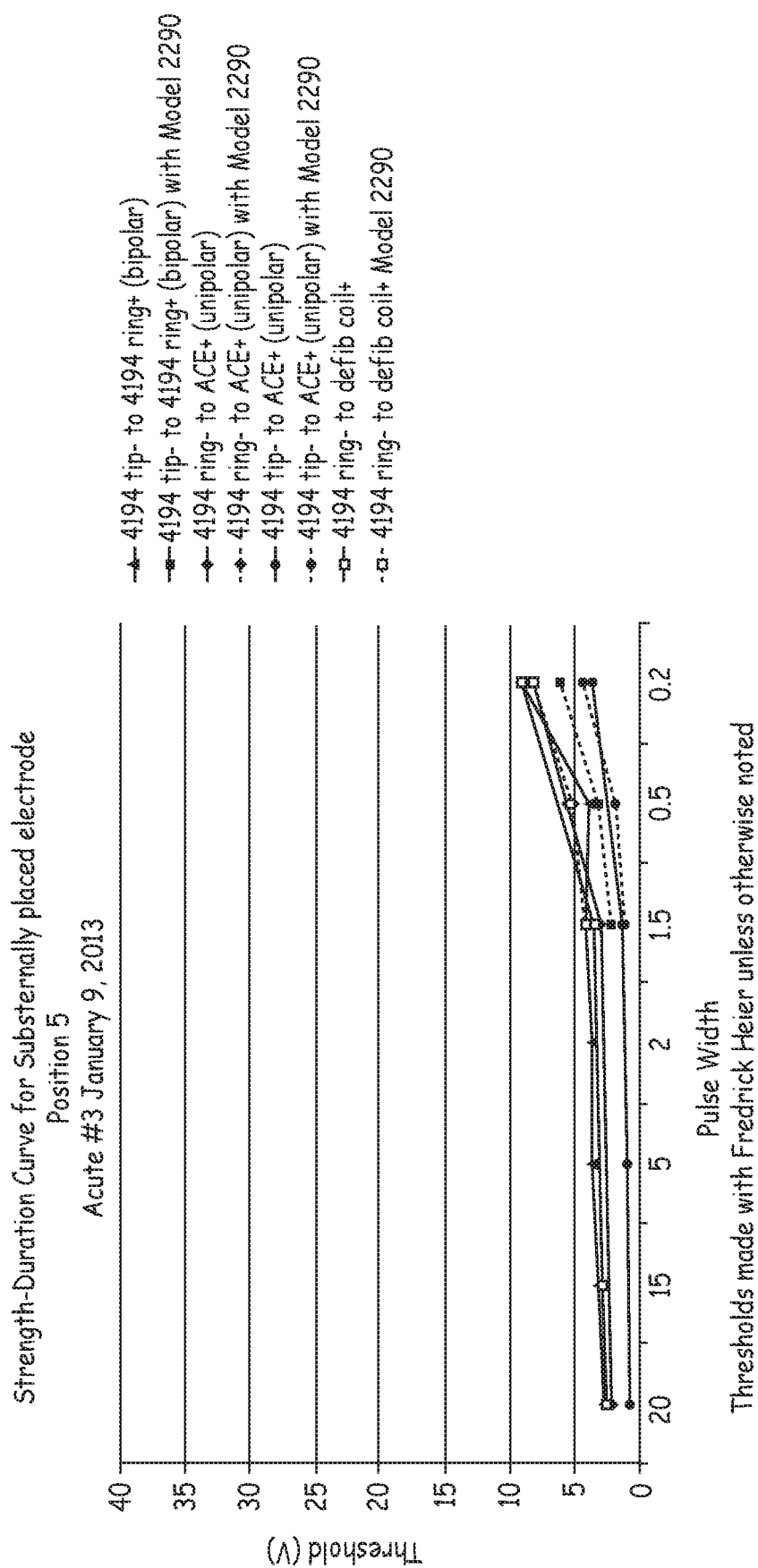
FIG. 8 is a graph illustrating strength-duration curves of electrical data from a third acute experiment with the lead positioned under the sternum at a third location.

FIG. 8 illustrates the strength-duration curve of electrical data from the third acute experiment when the 4194 lead tip was positioned under the sternum near the location of the $6^{th}$ rib. FIG. 8 shows the position dependence of the substernal/retrosternal electrode. When the pacing electrode is optimally located over the ventricular surface of the cardiac silhouette (as observed via fluoroscopy), pacing threshold is low. Low thresholds were very repeatable in this anatomical location, even at shorter pulse durations and in many different pacing configurations. Extracardiac stimulation generally was not apparent at low thresholds and longer pulse durations throughout this experiment.

All three acute experiments demonstrated the feasibility of pacing from a sub sternal/retrosternal electrode location. The lowest threshold results across the three acute procedures were 0.8 volts, 7 volts and 0.8 volts, respectively, with the second acute procedure involving an anatomical difference (pericardial adhesions) that tipped the ventricular surface of the heart away from its normal orientation with the sternum, resulting in higher pacing thresholds. However, for the purposes of anti-tachycardia pacing, conventional devices typically default to maximum output (8V at 1.5 ms) for ATP therapy delivery. Given this, even the 7V threshold obtained in the second acute experiment could be satisfactory for ATP therapy.

The ability to capture the heart at low pacing thresholds was dependent upon electrode position. As observed through these experiments, the substernal/retrosternal pacing electrode provide the best outcomes when positioned approximately over the ventricular surface of the cardiac silhouette, which is easily observed via fluoroscopy and encompasses a reasonably large target area for lead placement. In the third acute experiment, for example, capture was achieved at three separate positions, with the lead tip at approximately ribs 4, 5 and 6, all of which were near the ventricular surface of the cardiac silhouette.

Pacing thresholds increased with shorter pulse durations. In many instances, however, low pacing thresholds were obtained even at short pulse widths, especially when the substernal/retrosternal pacing electrode was positioned over the ventricular surface of the cardiac silhouette. In other instances, longer pulse durations (10-20 ms) were necessary to obtain capture or to achieve lower capture thresholds.

Across experiments, it was possible to pace from the substernal/retrosternal lead to an active can emulator positioned near the animal's side (unipolar) and also from the substernal/retrosternal lead to a subcutaneous ICD lead (unipolar). If a subcutaneous ICD system incorporated a pacing lead, placed substernally/retrosternally, for the purpose of anti-tachycardia pacing, both of the aforementioned unipolar pacing configurations would be available for a physician to choose from.

These experiments also demonstrated the ability to pace in a bipolar configuration entirely under the sternum (4194 tip (−) to 4194 ring (+), substernally/retrosternally), indicating that either a bipolar lead positioned under the sternum might be used for anti-tachycardia pacing purposes.

Overall, the results of these acute experiments demonstrate the ability to pace the heart from a substernal/retrosternal location, with the lead not entering the vasculature or the pericardial space, nor making intimate contact with the heart. The low threshold values obtained when pacing from a substernal/retrosternal lead location in these acute experiments suggest that pain-free pacing for the purpose of anti-tachycardia pacing in a subcutaneous ICD system is within reach.

Various examples have been described. These and other examples are within the scope of the following claims.

The invention claimed is:

1. An implantable cardioverter-defibrillator (ICD) system comprising:
   an ICD configured to be implanted subcutaneously in a patient;
   an implantable medical electrical lead that includes:
   an elongated lead body having a proximal end and a distal portion;
   a connector at the proximal end of the lead body configured to couple to the ICD; and
   one or more electrodes along the distal portion of the elongated lead body, the one or more electrodes including a defibrillation electrode, wherein the defibrillation electrode includes a first segment and a second segment, and wherein the first segment is separated from the second segment by a distance on the distal portion of the lead,
   wherein the distal portion of the elongated lead body of the lead is configured to be implanted substantially within an anterior mediastinum of the patient and the ICD is configured to deliver at least one of a cardioversion shock or a defibrillation shock to a heart of the patient via two or more electrodes electrically coupled to therapy circuitry of the ICD, the two or more electrodes including the defibrillation electrode.

2. The ICD system of claim 1, wherein the ICD is configured to deliver the at least one of the cardioversion shock or the defibrillation shock having an energy less than 60 Joules (J).

3. The ICD system of claim 1, wherein the ICD is configured to deliver the at least one of the cardioversion shock or the defibrillation shock having an energy between 40-50 Joules (J).

4. The ICD system of claim 1, wherein the ICD is configured to deliver the at least one of the cardioversion shock or the defibrillation shock having an energy between 35-60 Joules (J).

5. The ICD system of claim 1, wherein the distal portion of the lead is configured to be implanted substantially within the anterior mediastinum such that the defibrillation electrode is located over one of a cardiac silhouette of a ventricle of the heart as observed via an anterior-posterior (AP) fluoroscopic view of the heart.

6. The ICD system of claim 1, wherein the one or more electrodes includes at least one pacing electrode and the ICD is configured to deliver at least one of bradycardia pacing, antitachycardia (ATP) pacing, or post-shock pacing to the patient via the at least one pacing electrode.

7. The ICD system of claim 6, wherein the at least one pacing electrode comprises two pacing electrodes and the ICD is configured to deliver the at least one of the bradycardia pacing, the antitachycardia (ATP) pacing, or the post-shock pacing to the patient via a therapy vector between the two pacing electrodes.

8. The ICD system of claim 1, wherein the ICD is configured to deliver pacing pulses having pulse widths greater than two (2) milliseconds.

9. The ICD system of claim 1, wherein the ICD is configured to deliver pacing pulses having pulse widths between two (2) and three (3) milliseconds.

10. The ICD system of claim 1, wherein the ICD is configured to deliver pacing pulses having pulse widths between approximately one and a half (1.5) milliseconds and twenty (20) milliseconds.

11. The ICD system of claim 1, wherein the ICD is configured to deliver pacing pulses having pulse widths greater than two (2) milliseconds and less than eight (8) milliseconds.

12. The ICD system of claim 1, wherein the ICD is configured to deliver pacing pulses having pulse amplitudes between approximately one (1) and twenty (20) volts.

13. The ICD system of claim 1, wherein the distal portion of the lead is implanted substantially within the anterior mediastinum such that the defibrillation electrode is located substantially over an atrium of the heart and the ICD is configured to deliver a shock using the one or more electrodes to terminate atrial fibrillation (AF).

14. The ICD system of claim 1, wherein the distal portion of the lead is configured to be implanted substantially within the anterior mediastinum such that a therapy vector from the defibrillation electrode to the ICD is substantially across the ventricles of the heart.

15. The ICD system of claim 1, wherein the ICD is configured to deliver the at least one of the cardioversion shock or the defibrillation shock to the heart of the patient via the first segment and the second segment.

16. An implantable cardioverter-defibrillator (ICD) system comprising:
an ICD configured to be implanted subcutaneously in a patient;
an implantable medical electrical lead that includes:
an elongated lead body having a proximal end and a distal portion;
a connector at the proximal end of the lead body configured to couple to the ICD; and
one or more electrodes along the distal portion of the elongated lead body, the one or more electrodes including a defibrillation electrode,
wherein the distal portion of the elongated lead body of the lead is configured to be implanted substantially within an anterior mediastinum of the patient and the ICD is configured to deliver at least one of a cardioversion shock or a defibrillation shock to a heart of the patient via two or more electrodes electrically coupled to therapy circuitry of the ICD, the two or more electrodes including the defibrillation electrode,
wherein the one or more electrodes includes at least two sensing electrodes, wherein the ICD is configured to detect tachycardia using electrical signals sensed via the at least two sensing electrodes and to deliver the at least one of the cardioversion shock or the defibrillation shock to the heart of the patient via the defibrillation electrode in response to detecting tachycardia, and
wherein the at least two sensing electrodes comprise a first sensing electrode and a second sensing electrode, and wherein the first sensing electrode is separated from the second sensing electrode on the distal portion of the lead by the defibrillation electrode.

17. The ICD system of claim 16, wherein the ICD is configured to deliver the at least one of the cardioversion shock or the defibrillation shock having an energy between 35-60 Joules (J).

18. The ICD system of claim 16, wherein the distal portion of the lead is configured to be implanted substantially within the anterior mediastinum such that a therapy vector from the defibrillation electrode to the ICD is substantially across the ventricles of the heart.

19. An implantable cardioverter-defibrillator (ICD) system comprising:
an ICD configured to be implanted subcutaneously in a patient;
an implantable medical electrical lead that includes:
an elongated lead body having a proximal end and a distal portion;
a connector at the proximal end of the lead body configured to couple to the ICD; and
one or more electrodes along the distal portion of the elongated lead body, the one or more electrodes including a defibrillation electrode and at least two sensing electrodes,
wherein the distal portion of the elongated lead body of the lead is configured to be implanted substantially within an anterior mediastinum of the patient such that the defibrillation electrode is located substantially over a ventricle of the heart,
wherein the ICD is configured to detect tachycardia using electrical signals sensed via the at least two sensing electrodes and to deliver, in response to detecting the tachycardia, at least one of the cardioversion shock or the defibrillation shock to the heart of the patient via two or more electrodes electrically coupled to therapy circuitry of the ICD, the two or more electrodes including the defibrillation electrode in response to detecting the tachycardia, and wherein the ICD is configured to deliver the one of the cardioversion shock and the defibrillation shock having an energy less than 60 Joules (J).

20. The system of claim 19, wherein the distal portion of the elongated lead body of the lead is configured to be implanted substantially within an anterior mediastinum of the patient such that the defibrillation electrode is located substantially over the ventricle of the heart as observed via an anterior-posterior (AP) fluoroscopic view.

* * * * *